US007335020B2

(12) United States Patent
Castner et al.

(10) Patent No.: US 7,335,020 B2
(45) Date of Patent: Feb. 26, 2008

(54) LOW PROFILE SELF-LIGATING BRACKET ASSEMBLY AND METHOD OF USE

(75) Inventors: Daniel L. Castner, San Marcos, CA (US); David Winer, Vista, CA (US)

(73) Assignee: Lancer Orthodontics, San Marcos, CA (US)

( * ) Notice: Subject to any disclaimer, the term of this patent is extended or adjusted under 35 U.S.C. 154(b) by 107 days.

(21) Appl. No.: 11/323,978

(22) Filed: Dec. 29, 2005

(65) Prior Publication Data
US 2006/0228664 A1 Oct. 12, 2006

Related U.S. Application Data

(63) Continuation-in-part of application No. 11/102,541, filed on Apr. 8, 2005.

(51) Int. Cl.
*A61C 3/00* (2006.01)

(52) U.S. Cl. .............................................. 433/11; 433/8

(58) Field of Classification Search .................... 433/13
See application file for complete search history.

(56) References Cited

U.S. PATENT DOCUMENTS 5,908,293 A * 6/1999 Voudouris .................... 433/10

* cited by examiner

*Primary Examiner*—Cris Rodriguez
*Assistant Examiner*—Candice C Stokes
(74) *Attorney, Agent, or Firm*—Fulwider Patton LLP

(57) ABSTRACT

A self-ligating orthodontic bracket assembly with selectively removable self-ligation features is configured to provide a low profile to minimize labial-lingual prominence. A clip is configured to snap into the base of the bracket and close over the archwire slot to retain the archwire in the slot. The clip is easily moved to an open position when the archwire is changed out during routine treatment. The clip includes spaced apart arms that, along with the bracket tie-wings, straddle the most outwardly prominent site on the crown of the tooth thereby minimizing labial-lingual profile. The self-ligation capability is achieved without any increase in occlusal-gingival height or measial-distal width of the orthodontic bracket.

20 Claims, 23 Drawing Sheets

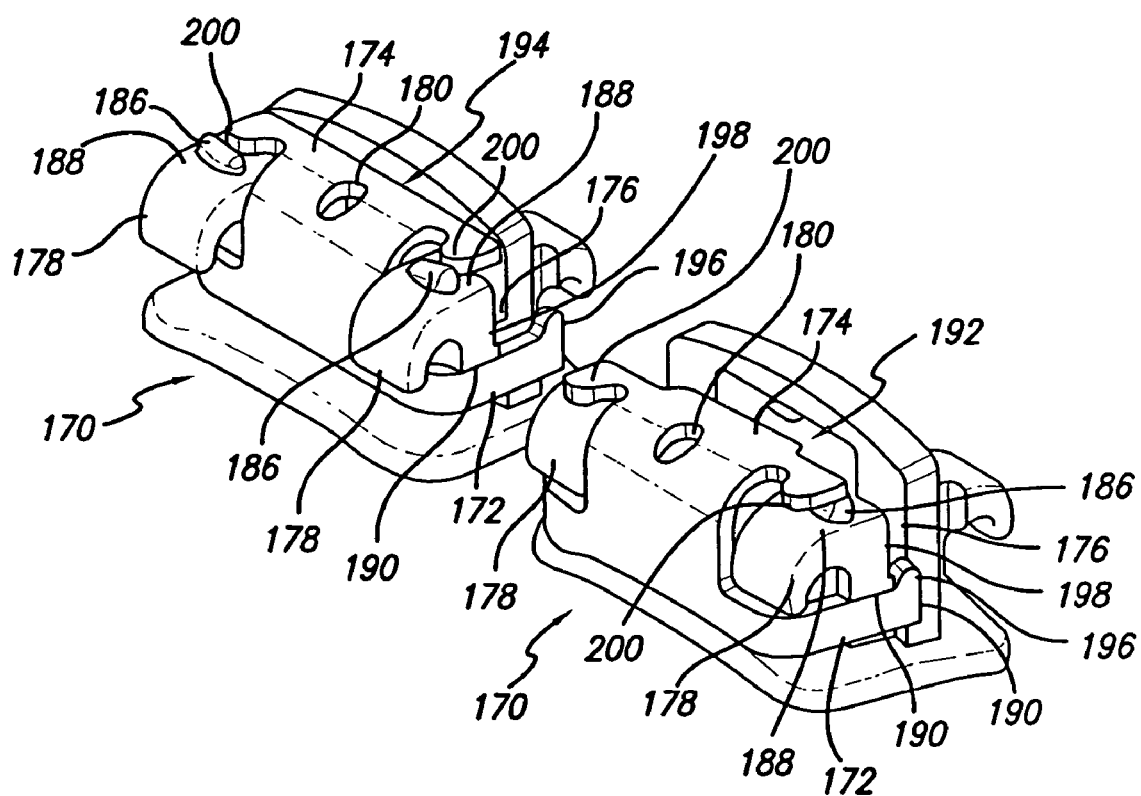

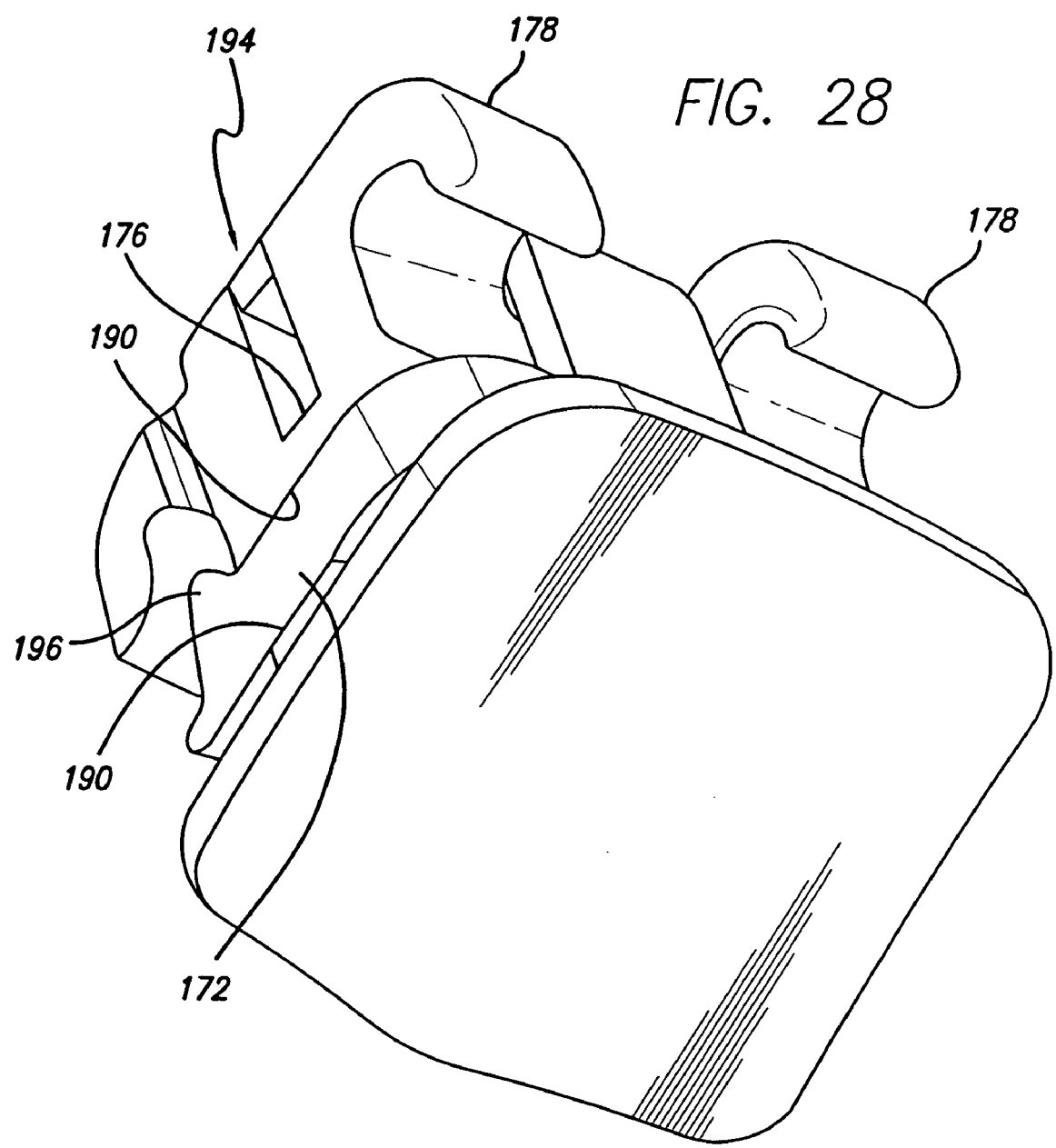

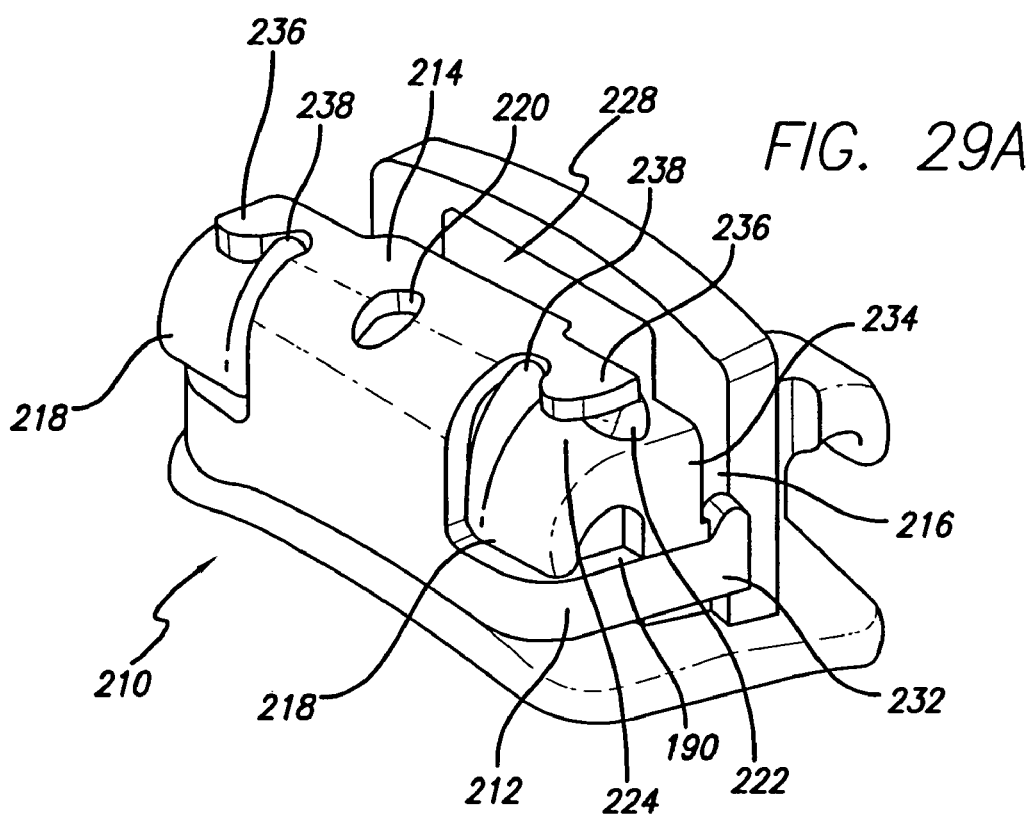
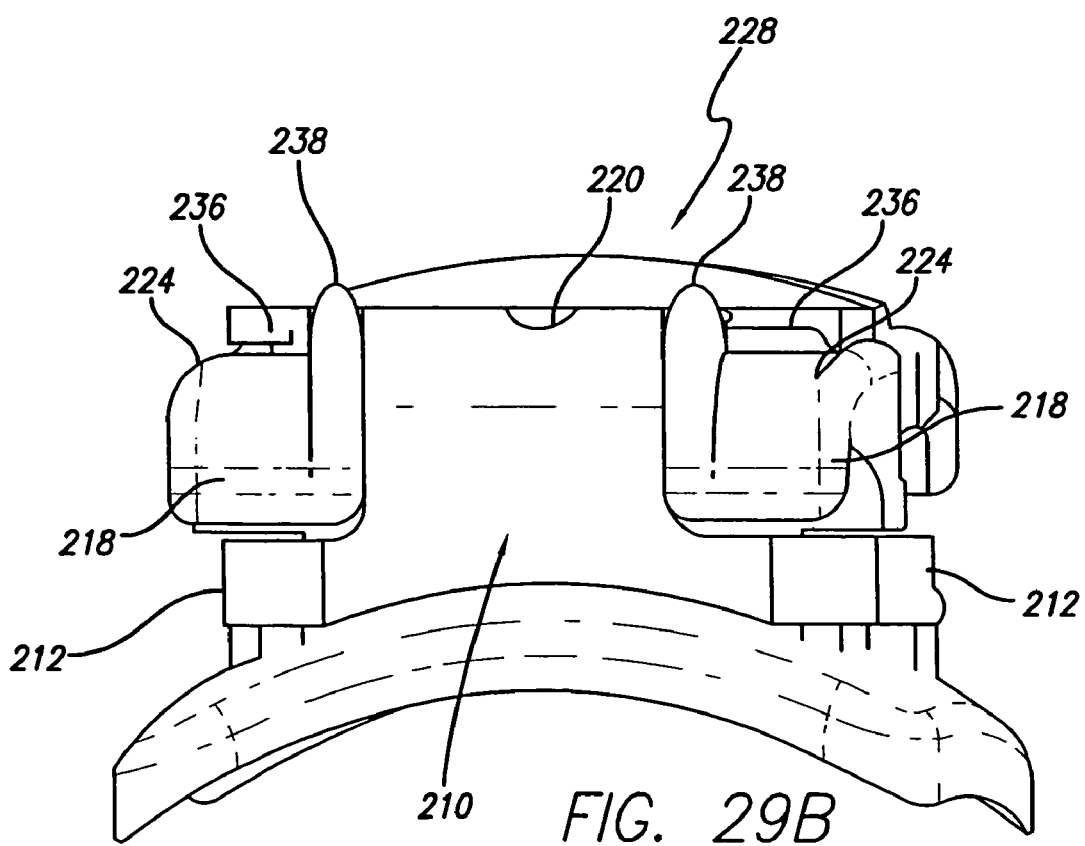

LOW PROFILE SELF-LIGATING BRACKET ASSEMBLY AND METHOD OF USE

CROSS-REFERENCES TO RELATED APPLICATIONS

This application is a continuation-in-part of U.S. Ser. No. 11/102,541 filed Apr. 8, 2005, the entire contents of which are incorporated herein by reference.

BACKGROUND OF THE INVENTION

The modern orthodontic bracket was developed by Dr. Edward Hartley Angle and became commercially available in the early 1900's. In spite of significant improvements in design, materials and manufacturing processes that have occurred since Dr. Angle's time, the biomechanical functioning of orthodontic brackets remains essentially unchanged.

A variety of orthodontic brackets have been designed over the years generally incorporating varied bonding bases connected to an orthodontic bracket body. The bonding base is connected to the bracket body by brazing or other means or a bracket can be fabricated as an amorphous one-piece unit. The bonding pad provides the interface for a mechanical bond between the bracket and the tooth. Once the brackets are bonded to the teeth, orthodontic wires are installed in the bracket's arch slots.

Normally a bracket or set of brackets are bonded to teeth and orthodontic wire(s) are engaged which will move teeth to predetermined positions according to a treatment plan created by an orthodontist. In order to engage the archwire in the arch slots of a series of brackets, it is common to use elastomeric, steel ligatures or other means of ligation to retain a sequential series of archwires typically needed during the course of orthodontic treatment. Conventional ligatures are looped or lassoed over the tie-wing structures of each bracket thus positively retaining the archwire in its corresponding slot in the bracket(s).

Central to the tooth-moving function of the orthodontic bracket is the archwire slot. The archwire slot is a horizontally oriented, outwardly opening trough spanning a bracket's labial or buccal face. Archslots should be understood as having a floor and two parallel walls perpendicular thereto, where the floor and walls define a rectangular configuration in cross section. Such a rectangular slot is intended to accept a correspondingly sized rectangular archwire. Orthodontic archwires, fabricated from resilient metallic materials generally are sized to matingly fill a bracket's archslot. In doing so, the archwire further provides continuity to the overall arch shape as it extends around the dental arch.

The rectangular and inter-fitting relationship between an archslot and its archwire is the defining characteristic of a system of orthodontic armamentarium used for a treatment methodology known as Edgewise Orthodontic Therapy. The Edgewise technique was developed by Dr. Angle and his contribution is substantial. Others, Including Dr. Lawrence F. Andrews have advanced the Edgewise bracket to its current high level of bioengineering To describe the biomechanical functioning of modern orthodontic brackets, the following description is provided: First, it must be understood that the orientation of the archslot as it transverses the face of a bracket is established for each type of bracket during the manufacturing process. Statistically determined values for torque, angulation, prominence and intrusion/extrusion are incorporated into the positioning of the archslot on a tooth-by-tooth basis. Second, reference for such statistical archwire positioning data is keyed off of both the archwire (as a datum) and off of anatomical guideposts on the teeth themselves. Ideally, such studied bioengineering of the archwire/bracket/archslot relationship leads to perfect alignment of the teeth and a perfectly straight and "spent" archwire at the end of treatment. As above, Dr. Lawrence Andrews advanced Edgewise Therapy in the 1970's. In orthodontics his treatment methodology is in fact well known as "Straight Wire" because of the functioning of such a system of rectangular slots and wires, ends in a straightened archwire at the conclusion of treatment.

The archwire and bracket system have an inter-working physiologic relationship. At the end of orthodontic treatment each tooth can be visualized as being in ideal relation to its adjacent teeth and its opposing teeth, with all the teeth aligned and in ideal positions according to an ideal archform. In such an ideal configuration, all of the walls of each bracket's archslot can be considered as being coplanar, defining a plane approximately parallel to the occlusal plane. Further, the center point of the floor of each archslot can be thought of as being tangent to an elegantly shaped natural archform. It is instructive to next consider such an orderly system of archslots as time is reversed, and the case is slowly returned to its pre-treatment condition. As this happens, the teeth all slide back to their original chaotic mal-positioned pre-treatment orientations taking the brackets attached to them with them. The archslots fall out of relation to each other and become as mal-positioned as the teeth they are attached to. The above exercise conceptually illustrates both the final objective and the starting condition of treatment in terms of archslot orientation.

It is the orthodontist maneuvering the archwire into the series of archslots at the beginning of treatment that provides the motive force for correction. As the archwire is forced into the arch slots via twisting and bending, energy is stored in the archwire as it is deflected this way and that. It is the slow dissipation of that stored energy that provides the continuous, gentle forces that desirably move the teeth into desired positions.

Not all archwires used in Edgewise Therapy are rectangular in cross-section. Edgewise orthodontic treatment calls for the use of a progressive series of archwires. Typically, smaller, round wires are used at the beginning of treatment. Such wires exhibit a low spring rate and low modulus, and are capable of handling the large bracket-to-bracket deflections encountered at the beginning of treatment without taking a set. Round archwires used early in treatment are not considered as being true Edgewise wires because being round in cross-section, they are incapable of imparting tortional correction forces against the flat slot walls and floor. In orthodontics, this type of force acting on the roots of the teeth is called "torque." To clarify this point, it must be understood that had such wires been used at the beginning of treatment, significant patient discomfort would have resulted, along with insult to the periodontal membrane surrounding the root of the tooth. Such round wires are nonetheless very capable of rapidly moving the significantly mal-aligned teeth in terms of intrusion and axial extrusion, rotation and tipping to begin the process of unscrambling the occlusion. The phase of treatment where the attending orthodontist may use a series of relatively small, but progressively larger and stiffer round wires is known as "first phase orthodontics" or the "leveling phase."

Later in the treatment sequence, after multiple round wires have been employed, an orthodontist may utilize the first of a series of true Edgewise wires. These archwires typically exhibit a higher spring rate and are therefore significantly stiffer. Such wires are incapable of spanning the large deflections encountered earlier in treatment without exceeding the effective physiological force range for tooth movement. To clarify this point, it must be understood that had such wires been used at the beginning of treatment, significant patient discomfort would have resulted, along with insult to the periodontal membrane surrounding the roots of the teeth anchored in the alveolar supporting bone. Further, such an archwire used inappropriately early in treatment would be likely to take a set and matallurgically yielding.

As can be appreciated, the use of larger, harder, square and rectangular archwires can only be initiated after significant orthodontic correction has been achieved. Importantly, since such wires do exhibit a square or rectangular cross-section, they are capable of beginning the positioning of the teeth in terms of torque. Torque is the motive force that swings of the root structure of the tooth though the supportive bone while holding the crown portion stationary. As described above, round wires are not capable of imparting torqueing forces to a tooth because they lack features needed to engage the Edgewise configuration of the archslot and therefore, they can only tip teeth around an unseen center of resistance in the supporting bone.

An orthodontist may begin the true Edgewise phase of treatment with an archwire with dimensions of 0.016×0.016 inch. As the 0.016 inch square archwire achieves a degree of response over a period of a few weeks, it will in turn be replaced by an archwire of slightly more robust dimensions such as of 0.017×0.021 inch. Again, Edgewise wires have mechanical properties that are distinctly different from the wires used at the beginning of treatment. The full-sized Edgewise finishing wires used during the final stages of treatment can be formed from highly work-hardened stainless steel and may exhibit a modulus of stiffness exceeding $3 \times 10^7$ and have a tensile strength approaching 300 KSI UTS.

As can be appreciated from the foregoing, and as related to the present invention, a significant portion of the entire time allotted for an individual patient's treatment is devoted to the routine steps of installing and removing a progressive series of archwires. Historically, changing an archwire and replacing it with the subsequent archwire has involved first cutting and removing typically twenty steel ligatures. Ligature wires are formed from dead soft stainless steel and are commercially available in diameters ranging from 0.009 to 0.012 inch. In addition to cutting and removing each tiny ligature wire from each bracket, a new ligature wire must be tied onto each of the typically twenty brackets. The tying step required by steel ligatures involves first lassoing the bracket, then tightly twisting, and then cutting off the excess. The remaining twisted section must be tucked under the tie-wings of the bracket to avoid laceration of the soft tissues of the tongue, cheeks and gums.

Orthodontic bracket bodies have been designed in a variety of geometries or shapes. The most common bracket used in orthodontic treatment has been a twin or Siamese-design, where there are at least two sets of tie wings located at each end of the archslot. These are referred to as the mesial tie wings and the distal tie wings. Ligatures typically pass from the occlusal tie-wings, up and over the archwire/archslot, extending to the gingival tie-wings where they are twisted, cut and tucked under the occlusal tie wings. In this manner ligatures hold the archwire down into the archwire slot. The tie-wings also support other structures such as hooks for elastics and the tie-wings themselves can serve as a sort of macro hook, accepting the loops of elastic chains and the like.

Additionally, other ligature systems fixate orthodontic wire into a bracket archwire slot to enhance orthodontic treatment. These ligature systems often require an alteration or variation of the bracket body design, pad design, slot dimensions or other bracket geometries traditional with a twin tie-wing bracket which have been commonly accepted and proven to work in providing optimal force delivery to complete orthodontic treatment.

Since such a large portion of an orthodontic patient's time in the orthodontist's chair is consumed by changing archwires in this manner, and since such routine archwire changes constitute a major cost to the orthodontic practice and contribute to the cost of treatment for the patient, much inventive effort has gone into identifying innovative chair-side systems that reduce the time and cost associated with archwire changing.

One innovation introduced in the mid-1970's was the commercial introduction of elastomeric ligatures. Injection molded from elastomeric polymers such as urethane, elastomeric ligatures form a tiny toroidal "o"-ring shape, and exhibit elastic properties so they can be stretched over the ligation features of an orthodontic bracket. Use of such elastomeric rings introduced some timesavings by eliminating the steps of cutting, tying and tucking of the traditional steel ligatures. Further, the elastomeric ligatures are available in a rainbow of colors as well as clear, black and glow-in-the-dark. Such an array reportedly adds a means for patient self-expression and an element of fun for orthodontic patients.

The use of elastomeric O-rings however introduce new difficulties and concerns. For example, they can discolor and stain and they can lose their tractive force capabilities as they absorb water in the mouth. In general, their biocompatibility, particularly as related to certain plasticizers they may contain to enhance their latex rubber-like properties has been brought into question in the orthodontic literature. Further, like the steel ligatures, the elastomeric ligatures require special dedicated instruments for placement, even though some orthodontists use standard instruments. In either case, any instruments for ligature placement must be sterilized after each use, thus requiring specific in-practice procedures which involve measurable cost.

The present invention is related to yet another path of innovation directed toward mitigating the time-consuming problems and cost associated with routine changing of archwires. Orthodontists have long sought out a bracket design that incorporates features where no ligature whatsoever is required to capture and retain the archwire in the archslot. This has led to the advent of the self-ligating orthodontic bracket. The present invention introduces desirable improvements over conventional self-ligating brackets as described below.

Prior art disclosing some form of self-ligating orthodontic brackets is found in U.S. Pat. Nos. 2,011,575; 3,772,787; 4,248,588; 4,492,573; 5,474,445; 6,071,118; 6,368,105; and 6,168,429.

In reviewing the general field of self-ligating brackets, both proposed and commercialized, it can be said that all versions that employ a vertically-sliding clip inherently compromise patient comfort. Patient comfort is compromised through the use of such brackets due to the fact that overall bracket prominence must be increased in order to accommodate the increased labial-lingual or buccal-lingual thickness of the bracket driven by the addition of a vertical slot. Being centrally located, such vertical slots incorporated into the bracket body are typically positioned adjacent to the labial-most or buccal-most point on the clinical crown of a tooth, and are therefore directly additive to the final position of the soft-tissue-contacting surfaces of such an orthodontic bracket.

Generally, commercial offerings of conventional Straight Wire Edgewise bracket systems are available grouped according to a bracket prescription. Such a bracket system or bracket prescription represents a discrete series of values for each bracket in the system. For example, a particular prescription may callout that for a maxillary cuspid bracket, its archslot shall be oriented according to a torque value of −2° and oriented to an angulation value of 13°. The same prescription may specify that the center of that bracket's slot floor is outset 0.023 inch from the enamel surface of the crown. The lateral tooth in the same prescription may call for an archslot that is oriented at 8° of torque, 9° of angulation, but outset from the lateral crown by 0.044 inch. Of importance for differentiation of the present invention, the reader should note the significant difference in the outsetting of the archslot, where in this example the cuspid archslot is outset only 0.022 inch whereas the lateral bracket's archslot is outset over half a millimeter further out from the tooth enamel.

A complete prescription will include torque, angulation and outset values for all of the set of twenty brackets. Such bracket system prescriptions are based on statistically determined norm values obtained from the human population, but many variant prescriptions have emerged influenced by research and the various investigators' assessment of stability, aesthetics, treatment protocol and so forth. Today, perhaps eighteen distinct prescriptions are commercially available to orthodontists. Accordingly, orthodontic manufacturers offer various types of bracket designs, each in multiple prescriptions.

As above, all prescriptions for orthodontic bracket systems include discrete values for the out-setting of the arch slot according to prominence values. Of all such values incorporated into such prescriptions, prominence is accepted as the most relevant value impacting patient comfort as well as the design continuity of the entire bracket system. To amplify this point, during orthodontic treatment brackets are bonded to the teeth and in position, they extend outward against the inside of the cheeks and lips. Subtle aspects involving the effective smoothness and particularly the prominence of the brackets greatly impact patient comfort/discomfort. The degree to which the presence of brackets irritates the opposing soft tissues has been demonstrated to directly correlate with bracket prominence. Pressure sores, erosion of tissue and even severe lacerations have been reported. In some cases these problems become so severe that orthodontic treatment must be curtailed all together. Because of the central concern that patients must be able to tolerate the orthodontic hardware in their mouths, commercially available bracket systems are bio-engineered with a very high emphasis placed on making the bracket system as low in prominence as the structural limitations of the materials and processes used to manufacture the brackets will permit.

As described above popular bracket systems inherently include certain brackets that are the shortest in stature (typically the cuspids or sometimes the mandibular second bicuspids) and conversely, they will contain the tallest brackets (typically the upper laterals). An engineer's task in designing such a bracket system is to focus on the most structurally challenged brackets of the system, which in turn are the lowest prominence (shortest) brackets. It is ultimately the structural considerations implicit within the design of these lowest brackets of the series that then predicts the height of the entire series. An explanation of this relationship follows.

As a bracket system is engineered, it is the structural considerations relating to the minimal thickness of (steel) material under the archslot required to avoid structural failures such as wing bending or archslot spreading or inward collapse during treatment that must be considered. Children at orthodontic treatment age (ten to fifteen years) live very active lives and are involved in sports and all sorts of rough activity. As orthodontic patients, they unfortunately pay little attention to instructions from their attending orthodontist to avoid putting certain types of things in the mouth (popcorn, frozen candy bars, crunching ice, etc.). The structural demands placed on orthodontic brackets and orthodontic armamentarium can be severe. Metallurgical strength and structural stiffness needed to withstand such destructive forces are measured in terms of the unit strength of the material along with its modulus, tensile and compressive strength properties.

Advanced biomedical alloys are used in the fabrication of orthodontic armamentarium, including work hardened stainless steel, titanium, chromium-cobalt alloys and the heat-hardenable alloys of stainless steel such as 17-4 and 17-7 PH. Overall, orthodontic brackets are highly engineered to be as low in prominence as such specialty metals will permit. Distortion of brackets during treatment resulting from trauma mastication, bruxism, mechanical interference between teeth and other brackets, and distortion caused by such things as "sports accidents" all must be anticipated from a structural design standpoint. Again, the "Achilles heel" of orthodontic brackets is the thin structure under the archslot. It is on this area that destructive forces are concentrated and it is at this point that a bracket may structurally yield to those forces. To appreciate the advantages of the present invention, it must also be understood that the amount of structure under the archslot also directly predicts the overall height of a bracket. The reader can then appreciate that overall bracket design is driven by some very demanding design criterion that are directly at odds with each other. If brackets could be designed with higher prominence, they could much more easily withstand destructive forces but their higher prominence would result in unacceptable levels of patient discomfort.

So, any bracket system's design is driven by those particular brackets within its prescription that are most vulnerable to distortion and structural failure. Stated differently, it is the lowest bracket in the system that defines the "structural minimum" of the system, and in doing so, it thereby defines the height of all of the rest of the brackets. Stated differently again, after the structural requirements have been established for the structural minimum of a system of brackets, the prominence values for the rest of the brackets of greater prominence can be established according to the exact outset values of the bracket's prescription. It can be said that for all of these reasons then, it is paramount that orthodontic brackets be designed at the absolute minimum prominence consistent with structural survivability in the mouth.

Since prior art self-ligating bracket designs center the vertically siding clip directly over the labial-most or buccal-most point on the tooth crown, the thickness of the clip itself, and the labial-lingual dimension of its vertical channel contribute additively to what engineers call "material stack." For example, the dimensions of a vertical slot, passing in a occlusal-gingival direction may be 0.012 inch in a labial-lingual dimension. Establishing the thickness of the bracket material between the ceiling of such a vertical slot and the floor of the main horizontal archslot involves considerations of stresses on brackets during treatment as described in detail above. This area of the bracket's structure represents the location of the Achilles heel where the destructive forces are concentrated. In the case of prior art self-ligating brackets with vertically sliding self-ligation features, the body of the bracket must be correspondingly outset from the tooth to accommodate these features between it and the tooth surface.

Unlike the present invention, in order for prior art brackets to gain the function of self-ligation, they become inherently higher in prominence by at least the labial-lingual dimension of the vertical slot through which their clip slides.

These prior art ligature systems are designed to fixate or hold an archwire into a bracket slot without requiring the use of separate elastomeric or wire ligatures to fixate or attach an archwire into a bracket slot. This allows the orthodontist to keep an archwire ligated or fixated into a bracket archwire slot without changing and applying separate elastic or steel ligatures. This allows for some time savings and clinical efficiencies during the course of orthodontic treatment. Such advances, however, can ultimately prove useless if self-ligation features drive the height of a bracket system to an unacceptable level where a patient cannot tolerate them.

Some of the enhanced mechanical advantages promulgated by the inventors of prior art self-ligating bracket designs include the fact that self-ligating features that engage only the bracket body and thereby do not come in contact with the archwire during treatment greatly reduce bracket friction. Such a lack of direct archwire contact is claimed to reduce or eliminate mechanical friction caused by the tendency of conventional ligatures tendency to forcefully pull an archwire hard against the arch slot floor. The orthodontic literature contains many reports reinforcing these claims that bracket to archwire binding slows tooth movement and adds to the overall length of a patient's treatment. The present inventive assembly likewise does not force the archwire against the archslot floor and in fact, an archwire contained within the present inventive bracket remains unrestricted in all axes other than the confines described by the rectangular volume of the archslot.

Even though many prior art self-ligating bracket features may desirably reduce friction and mechanical binding, they nonetheless require a deviation away from the useful twin or Siamese-type bracket design that incorporates two sets of tie-wings. Such prior art self-ligating designs are limited and incapable of delivering certain corrective forces to the teeth. Some of these alterations are designed to allow the archwire ligation mechanism space to be incorporated as part of the orthodontic bracket and work to ligate the archwire into the archwire slot. These alterations can compromise the benefits of utilizing a twin orthodontic bracket.

Some of the current self-ligation brackets have designs that are not easy to use during the course of orthodontic treatment. They can be harder to space to disengage the orthodontic wire during treatment or to allow for the next sequential archwire to be space-engaged in its place. Therefore special instruments may be needed to be used to open and sometimes close the ligation mechanisms to allow for archwires to be removed and replaced to progress the course of orthodontic treatment.

The self-ligation capability of some known self-ligating bracket systems works efficiently only later in treatment after the teeth have been sufficiently aligned. High angles of archwire deflection as an archwire enters and exits the archslot of such a bracket cannot be accommodated. Highly deflected archwires, such as those typically used early in treatment can circumvent such self-ligation features thereby causing special problems for the orthodontist and greatly compromising the otherwise positive advantages of self-ligation.

Some of the current self-ligation brackets require additional springs or inserts to be incorporated into the design in order to facilitate the ligation function. This allows for the ligation mechanism to stay open or closed reliably and predictably during the course of treatment.

Some of the current self-ligation brackets do not allow for the ligation cover to be removed during orthodontic treatment. Additionally, if the ligation cover comes off the bracket body for some reason during treatment, the ligation cover can not easily be put back in its place to continue the course of treatment without having to remove the entire bracket from the tooth and replace it with a new bracket.

Prior art bracket assemblies can also have clips that undesirably pop open or can be difficult to open or close.

One difficulty of prior art self-ligating brackets is that they tend to become encrusted with calculus, plaque and oral bacteria. A central vertical channel in prior art brackets tends to provide a particularly good harbor for bacteria because of little flushing by saliva and the propensity for plaque to become established and to harden. Such a configuration makes it impossible to get a toothbush in place to reach such small internal features. It is known that all too often, the clips of prior art self-ligating brackets become bound up and locked in place due to buildup of hard plaque deposits. Patients having these types of self-ligating brackets are often instructed to rinse frequently with an anti-plaque rinses to help reduce the frequency of jammed clips.

On the other hand, the two channels of the present invention, being on the external mesial and distal edges of the bracket are much more accessible, and are therefore irrigated with saliva much more readily. Being on the outside surfaces of the bracket, these features can be reached by a toothbrush or irrigated with a water pik. This aspect of the present invention greatly reduces the undesirable likelihood of the clip becoming locked in place due to plaque deposits. The brackets of the present invention provide a greatly reduced potential for compromised oral hygiene during treatment due to the lack of features that can provide and harbor oral bacteria.

SUMMARY OF THE INVENTION

The present invention relates generally to a two-part orthodontic bracket of the Siamese or twin-type design that incorporates self-ligation features. The self-ligation function is achieved by inclusion of a separate, sliding heat treated and formed ligation cap that functions to selectively open and close access to the bracket's archslot by moving between a locked closed and a locked open position in a generally vertical, occlusal-gingival axis. Bracket features accommodative of such a sliding cap include a pathway or channel system located on the mesial- and distal-lingual edges of the bracket body and also include a cap-accommodating relief and positive stop on the incisal surface of the bracket body.

The metal clip is configured to hold the orthodontic archwire into the bracket archslot. The formed and heat treated clip is produced separately from the bracket and once installed onto the bracket body, it is held in place by inwardly biased paws on arms of the clip that slide in paw/arm-accommodating channels in the bracket base. The clip travels within a range of motion defined by a locked closed position and a locked open position, the range of travel being determined by the geometry of the face and stem of the bracket. A pair of locking ridges protrude from the mesial and distal gingival tie wings to secure the clip in a locked position. A pair of clip travel stops on the mesial and distal incisal tie wings hold the clip in a locked open position. The "locking" action that occurs at each end of this range of motion is also created by the inwardly biased resilient spring properties of the clip being loaded or unloaded in a mesial-distal axis unlike conventional self-ligating detent structures required for a snapping-closed and snapping open in a labial-lingual axis. Such features, if oriented in a labial-lingual axis can impact patient comfort by raising the prominence of the bracket, which the present invention avoids. These travel limiting features allow for the clip to not travel past the point of failure or beyond the body of the bracket tie wings which can make it easier for the clinician to manipulate during treatment.

The clip utilizes two channels for transporting the clip from its slot-open position to its slot-closed position with such channels being located at the lingual, mesial and distal periphery of the bracket body. This allows the prominence of the archslot to be as low as any non-self-ligating bracket because the arm structures of the clip "straddle" the most prominent portion of the crown. This configuration should be contrasted to conventional self-ligating brackets that are configured to "stack" the self-ligating structures literally directly on top of the most prominent point on a tooth's crown. The present inventive bracket and clip assembly then accommodates self-ligation capability with no sacrifice to, or compromising of the lowest possible prominence of the bracket.

The two arms of ligation clip "straddle" the labial-most point on the crown of the tooth, and in doing so, fall lingually to that point and provide for the lowest possible profile.

In another embodiment, the labial surface of the bracket, in the area of the archslot, is slightly higher in the labial-lingual direction than is the labial surface of the clip. In this embodiment, the clip has protrusions that correspond to recesses in the archslot to lock the clip in the closed position over the archslot. In another embodiment, the clip is locked into a closed position and held there by a pair of locking ridges on the labial surface of the tie wings. This prevents the clip from prematurely opening, yet allows the orthodontist to slide the clip over the locking ridges to move the clip to an open position without passing a point of slipping off the bracket body.

BRIEF DESCRIPTION OF THE DRAWINGS

These and other features, aspects and advantages of the present invention are described with reference to the drawings of preferred embodiments, which are intended to illustrate, but not to limit the present invention.

FIG. 21 is a perspective view of an orthodontic bracket assembly having a self-ligating clip positioned in the clip open position.

FIG. 22 is a perspective view of an orthodontic bracket assembly having a self-ligating clip positioned in the clip locked position and covering the archwire slot.

FIG. 28 is a bottom perspective view of an orthodontic bracket assembly depicting a self-ligating clip in a self-locked position.

FIG. 29A is a top perspective view of an orthodontic bracket assembly depicting a self-ligating clip positioned in a clip open position.

FIG. 29B is a front end view of the orthodontic bracket assembly of FIG. 29A.

DETAILED DESCRIPTION OF THE PREFERRED EMBODIMENTS

The new bracket and ligation method provides for a traditional twin or Siamese-type bracket with two distinct pairs of ligation wings to be manufactured by injection molding, sintering, machining or casting. This bracket body incorporates the popular Siamese-type bracket configuration for enhanced rotation-correction capabilities and can be utilized as such by an orthodontist even in the presence of self-ligation features.

Figure 1:
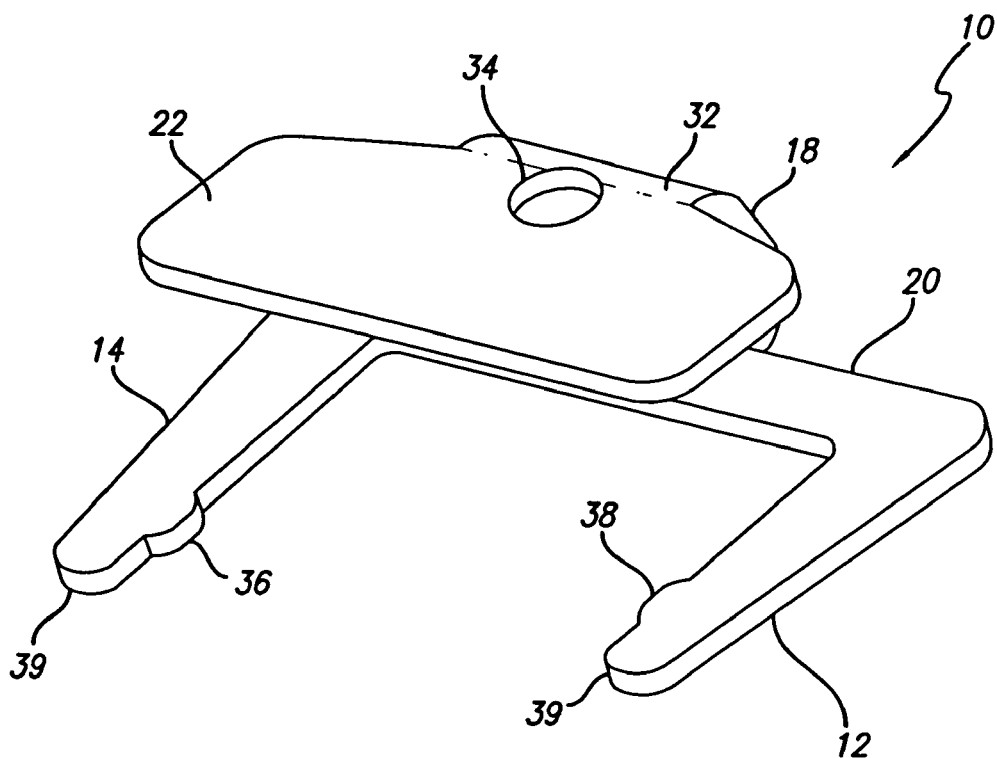
FIG. 1 is a perspective view of a self-ligating clip.
Figure 2:
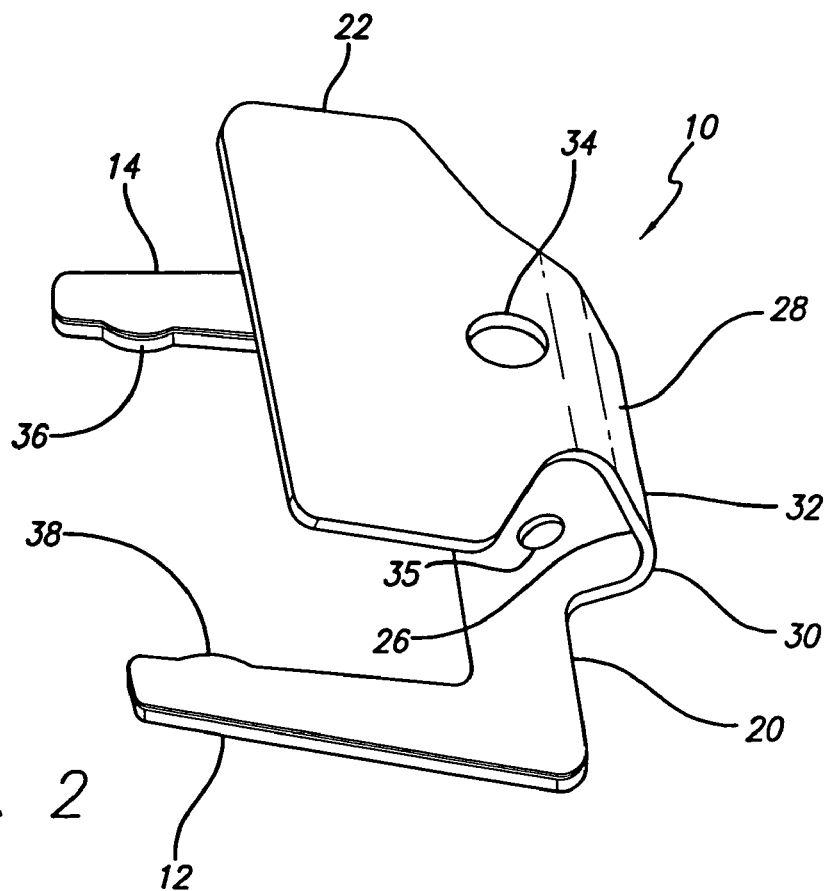
FIG. 2 is an angled side view of the self-ligating clip.
Figure 3:
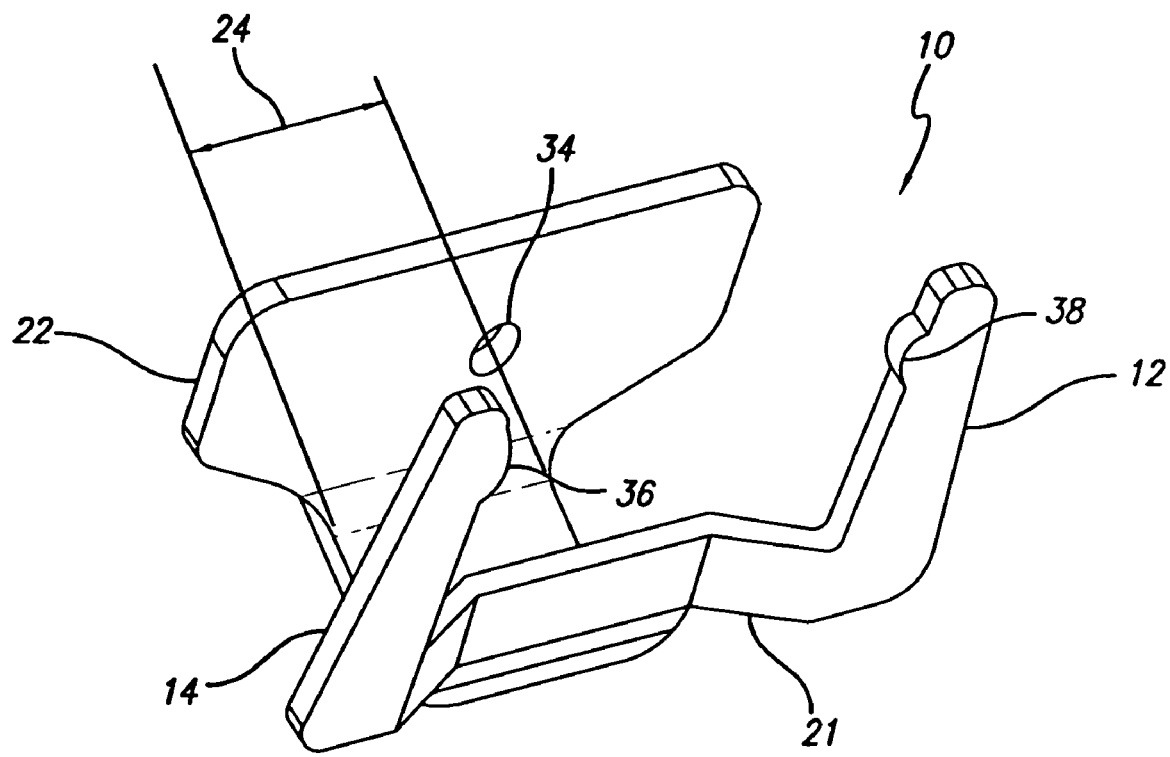
FIG. 3 is a perspective view of the bottom of the self-ligating clip.

In keeping with the invention, as shown in FIGS. 1-3, a clip 10 has a U-shaped configuration and includes a pair of arms 12,14 that engage an orthodontic bracket 16 (not shown in FIGS. 1-3). The arms are attached to a clip spine 18 by a cross-bar 20 or preferably, by bilateral crossbar risers 21 (FIG. 3). The clip spine extends generally labially from the crossbar or from a sternum if bilateral crossbar risers are present, and then widens laterally to form a slot cap 22. The overall resiliency of the clip can be controlled by controlling various factors of the clip's design and processing during manufacture, several of which are a spine width 24 and spine curvature 26. Thus, by increasing spine width effective stiffness of the clip increases, providing the clip with relatively greater archwire retention force when installed on the bracket. Similarly, if increased spring-like flexibility is deemed desirable, the spine width is reduced. Also, the spine curvature affects the archwire retention force of the clip on the bracket. The spine curvature can be a smooth and uniform radius, a compound radius, or multiple radii 28,30 with a flat section 32 between the radii. Further, the choice of metal alloy and its metallurgical processing used to form the clip all allow for tailoring the mechanical properties of the clip as needed. The clip also includes an aperture 34 in the cap which is a feature used for opening and closing of the clip while in place on the bracket. The arms 12,14 have paws 36,38 for engaging the bracket as will be described. The arms have tips 39 that extend gingivally beyond the paws.

Figure 3A:
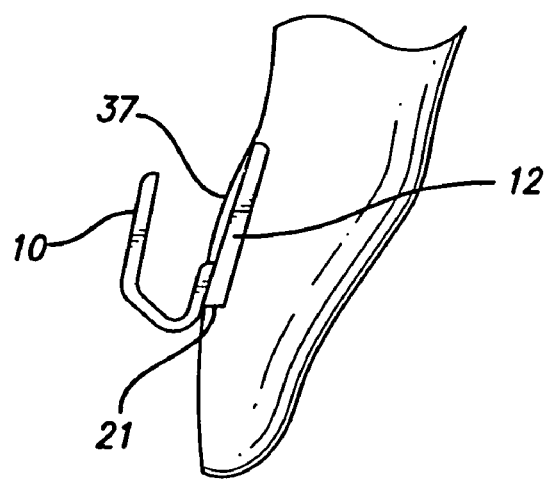
FIG. 3A is a side elevation view of the self-ligating clip on the tooth illustrating the lowest possible prominence or profile of the clip.

As shown in FIGS. 3 and 3A, an important feature of the invention relates to the low profile of clip 10. More specifically, when the clip is mounted on an orthodontic bracket (not shown in FIGS. 3 and 3A), and the orthodontic bracket is mounted on the tooth, the position of the arms 12,14 is such that the arms straddle the Andrews site 37 located on the outwardly-most prominent point on the crown of the tooth. More specifically, the spacing of arms 12,14 and the fact that there is a cross-bar riser 21, permits the arms to straddle the Andrews site 37, thereby presenting a much lower profile clip 10 relative to prior art clips. By low profile it is meant that in combination, these features enable self-ligation capabilities without requiring any increase in labial-lingual profile which promotes patient comfort. The low profile of the clip, and hence the orthodontic bracket, provides a much more tolerable bracket and clip to the patient which is important for patient comfort during orthodontic treatment.

Figure 4:
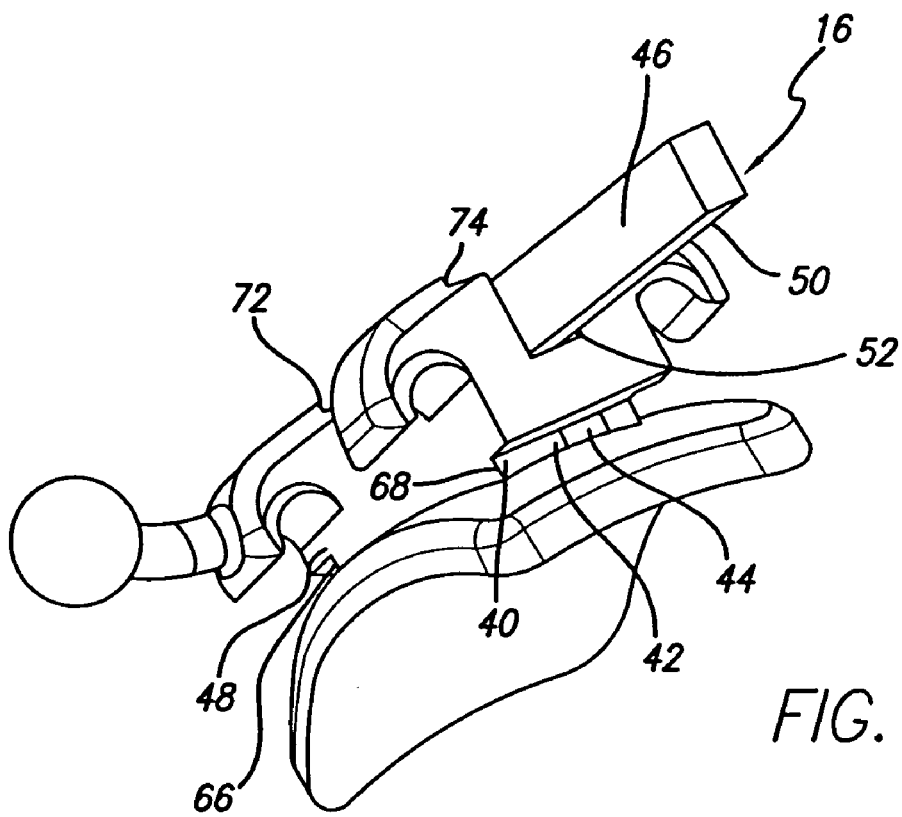
FIG. 4 is a perspective view of the orthodontic bracket assembly.
Figure 5:
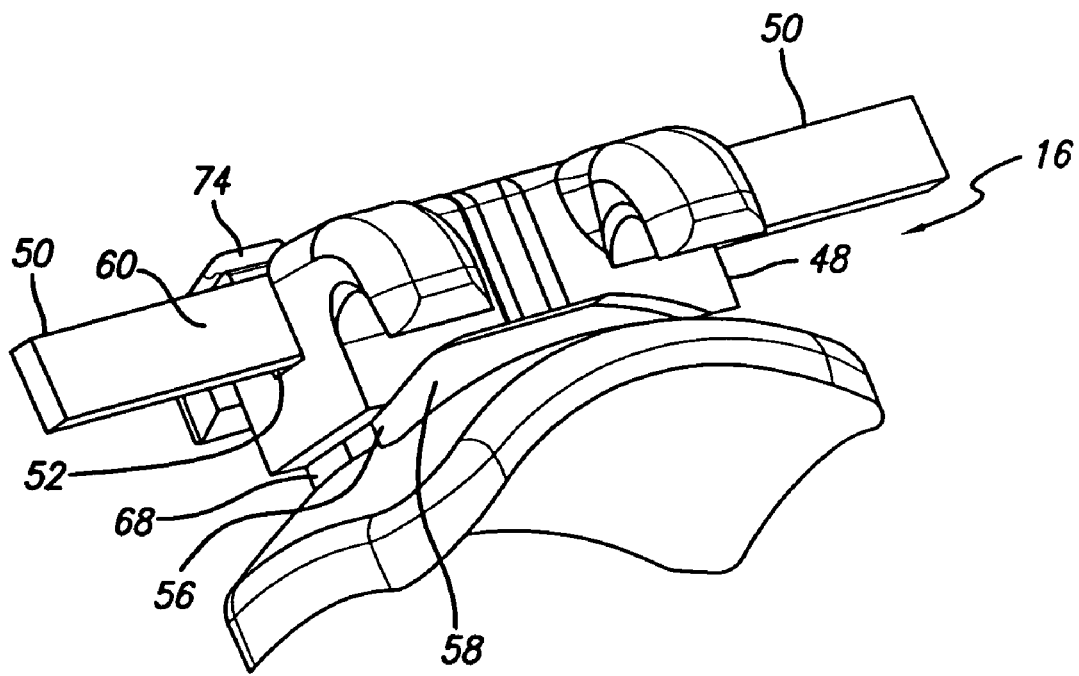
FIG. 5 depicts a perspective view of the orthodontic bracket assembly showing the clip transport ways.

As shown in FIGS. 4-5, the bracket 16 has an undercut relief area 40 in the base of the stem of the bracket body to form a pathway 42. Also, there are undercut relief areas on each end of the bracket. This pathway incorporates a detent 44 on the mesial end 46 and distal end 48 of the bracket. These pathways are intended to slidingly receive the arms of the clip 10 and allow the archwire 50 to be selectively retained in or released from the bracket archslot 52 as required during orthodontic treatment to remove and replace an archwire.

Figure 6:
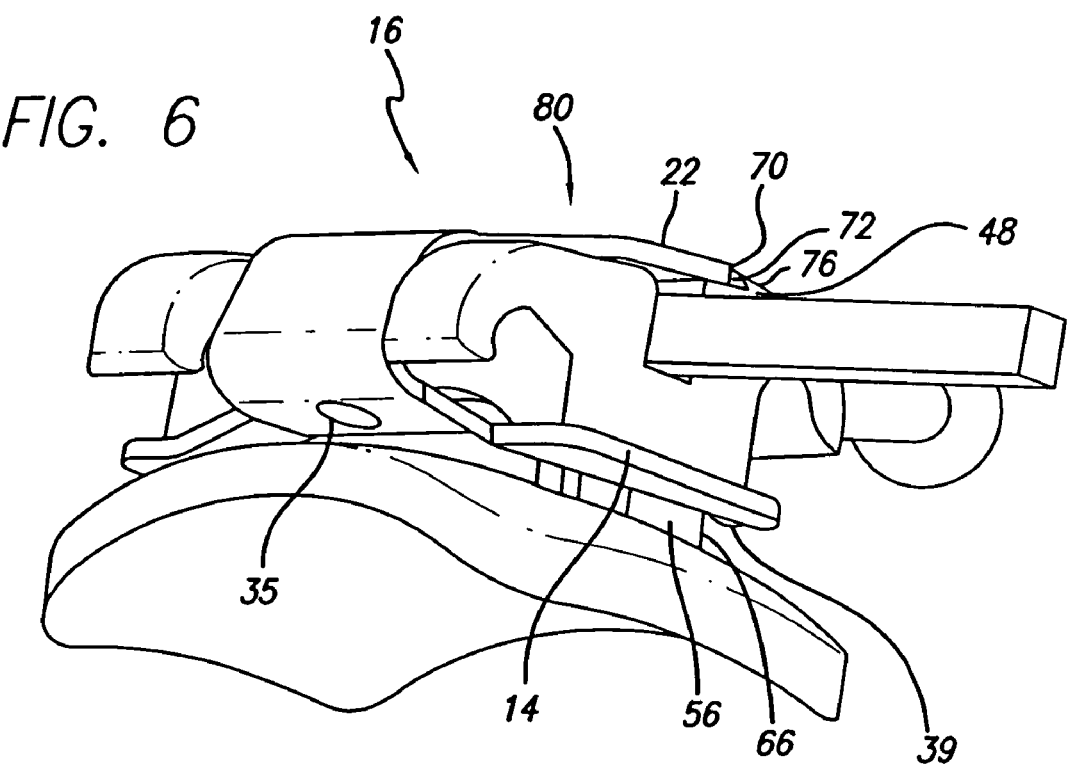
FIG. 6 is a perspective view of the orthodontic bracket assembly with the clip positioned in the locked-closed position.
Figure 7:
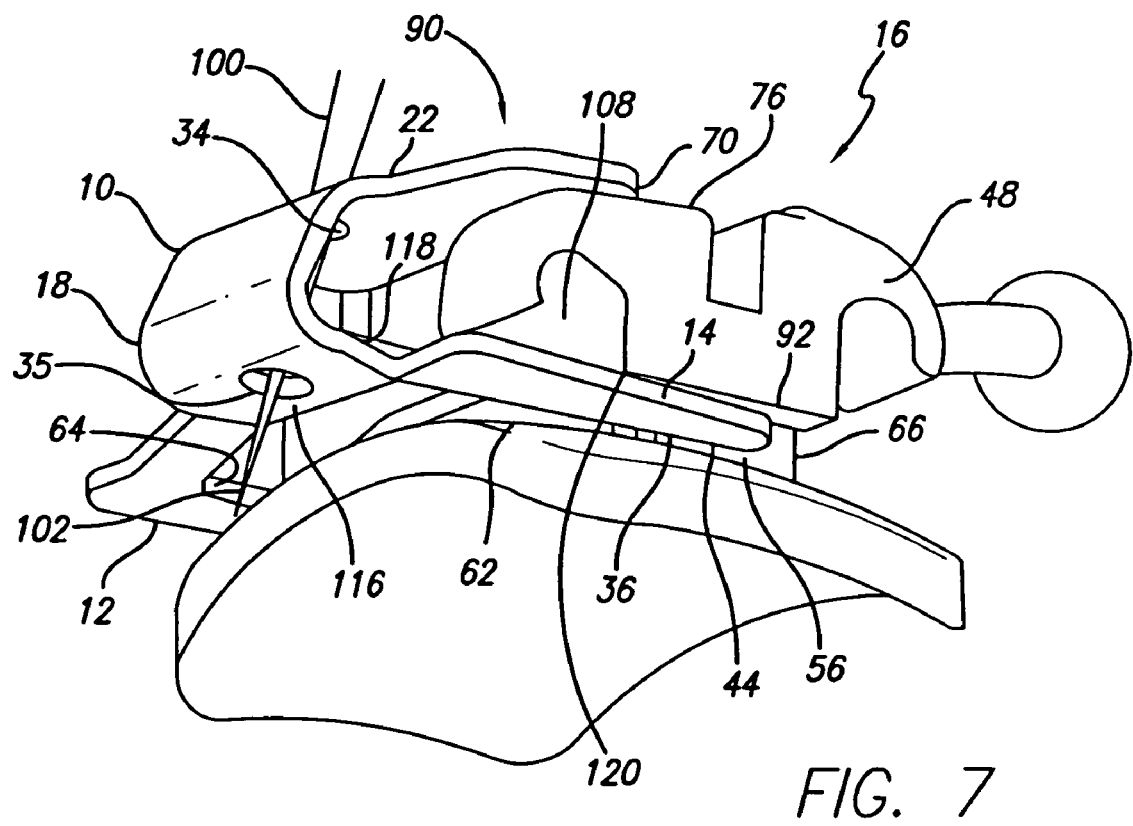
FIG. 7 depicts a perspective view of the orthodontic bracket assembly where the self-ligating clip is in the locked-open position.

Referring to FIG. 6, the clip 10 is held in a locked closed position 80 by the metallurgically-induced spring properties of clip 10, which resiliently bias the paws inward around the locked-closed locking corners 66,68 on the gingival corners of the bracket body. In the locked open position 90, the paws 36,38 of the arms fall into detents 44 in the clip transport ways 56 of the bracket body. When locked closed, the paws 36,38 fall similarly around the locked closed corners 66,68 of the bracket body.

In one embodiment, as shown in FIGS. 4-7, a clip transport way 56 on the mesial end 46 and distal end 48 of the bracket 16 extend occlusal-gingivally at the occlusal edge 58 of the bracket body 60. The transport ways 56 matingly accept the arms 12,14 of the clip 10. As the clip slides into the locked-closed position, paws 36,38 located on inward-facing surfaces 62,64 of the arms are allowed to unload inwardly once they pass gingivally around the closed position locking corners 66,68 of the bracket body. Resistance to outward loading due to the spring qualities of the clip material causes the clip to be aggressively held closed by the caming action of the inwardly-facing paws tangentially contacting and gripping the closed position locking corners. The gingival edge 70 of the slot cap 22 comes into contact with the clip travel stops 72,74 located on the labial surface 76 of the bracket 16. This occurs simultaneously as the clip "pops" into its locked-closed position 80, shown in FIG. 6. The clip travel stops 72,74 add stability to the clip slot cap and help the clip stay in place and to resist the potentially destructive forces of mastication.

The clip 10 of the present invention can be formed from any metallic alloy having a sufficiently high modulus of elasticity. When the clip is locked-closed and locked-open, the bending forces described above should not plastically deform the arms 12,14. Rather, the arms are resilient and safely flex so that the clip can be moved from the locked-close to the locked-open position, the archwire removed and replaced, and the clip moved back to the locked-closed position to retain the archwire in the archslot. Suitable metals capable of exhibiting appropriate mechanical properties include stainless steel alloys, titanium, cobalt-chromium, Nitinol, NP35N, and superelastic or pseudoelastic alloys and/or shape memory alloys. The orthodontic bracket is formed from biocompatible metallic alloys, composite materials or ceramics all of which are well known in the art.

The force required to release the grip of the clip paws 36,38 on the bracket 16 closed-position 80 and to move the clip toward a locked-open position 90 is regulated by the spring properties of the clip material and by control of the dimensional inter-fit between the arms 12,14, paws 36,38, and the clip transport ways 56 and 58. By locked-open position it is meant that the arms of the clip are engaged and locked into the detents 44 of the clip transport ways 56, and the slot cap 22 is open and not covering the archslot 52. The arms are held in a coincident or co-planar relationship with the ceiling 92 of the clip transport way by the sizing and shaping of the clip spine 18, and the orientation of the slot cap 22 as it rides across the labial surface 76 of the bracket.

Figure 8A:
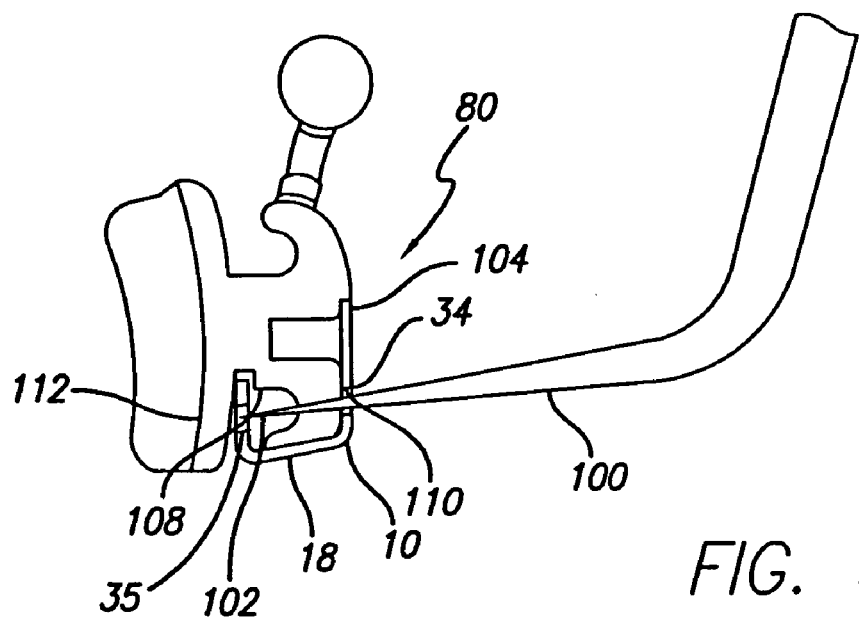
FIG. 8A depicts a partial cross-sectional side view of the orthodontic bracket assembly with a scaler moving the self-ligating clip.
Figure 8B:
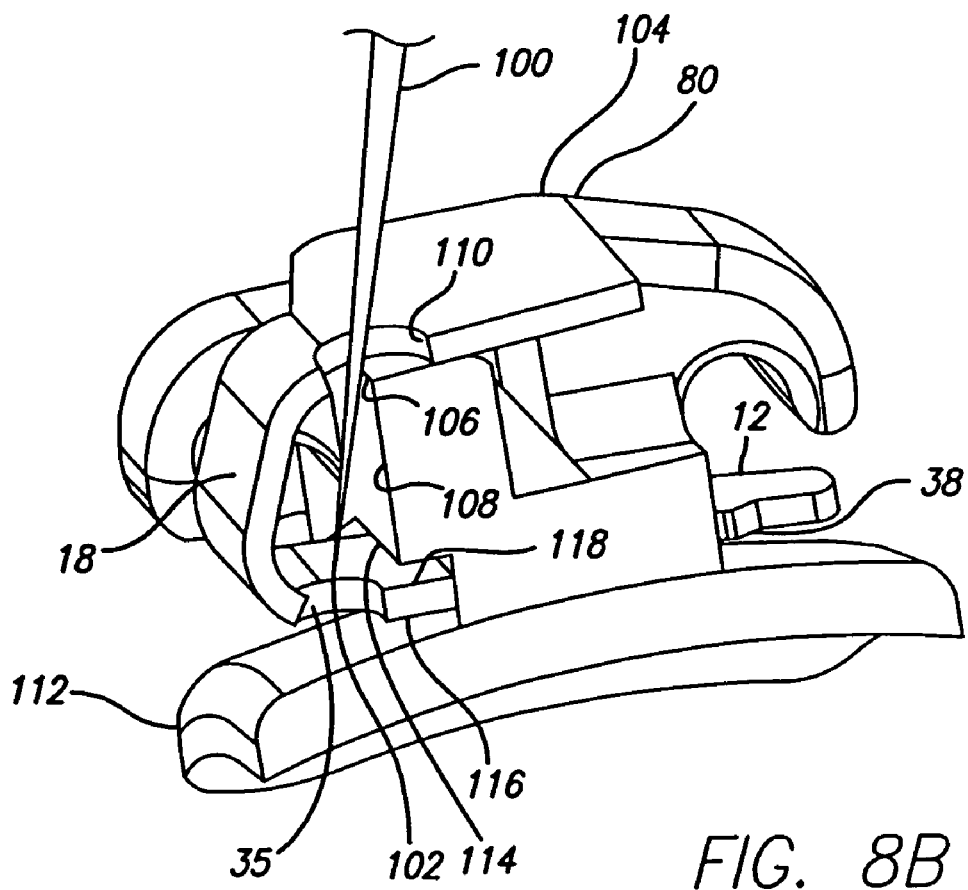
FIG. 8B depicts an enlarged cross-sectional side view of the orthodontic bracket assembly with the self-ligating clip in the locked-closed position and the scaler tip moving the clip toward an open position.
Figure 9:
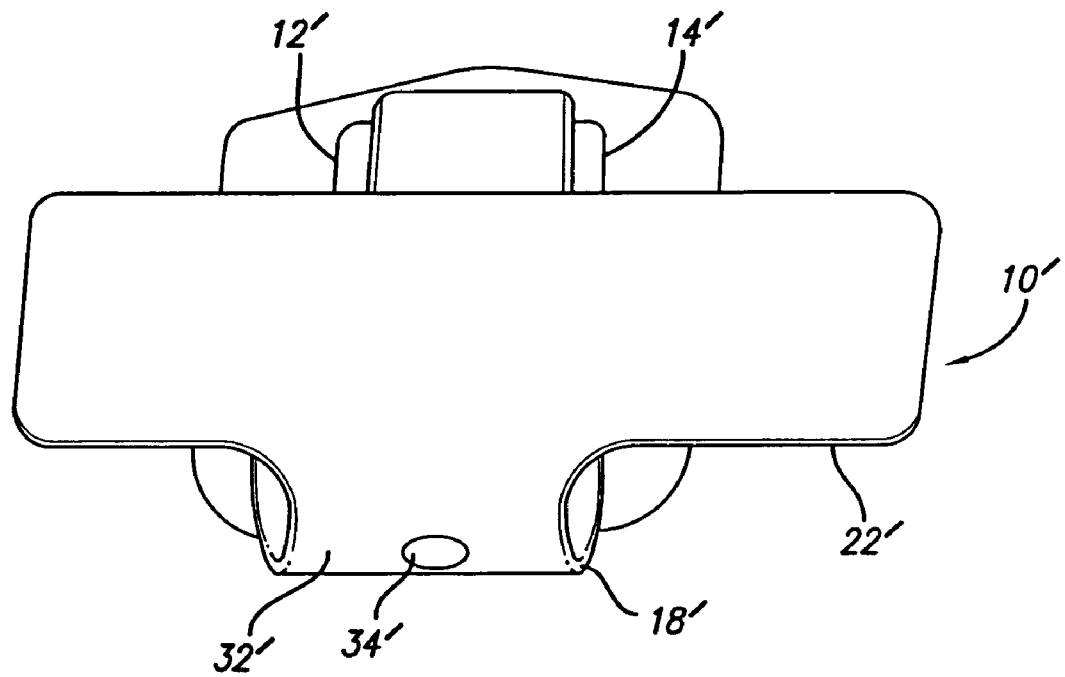
FIG. 9 depicts a top view of a single wing orthodontic bracket assembly with a self-ligating clip mounted thereon.
Figure 10:
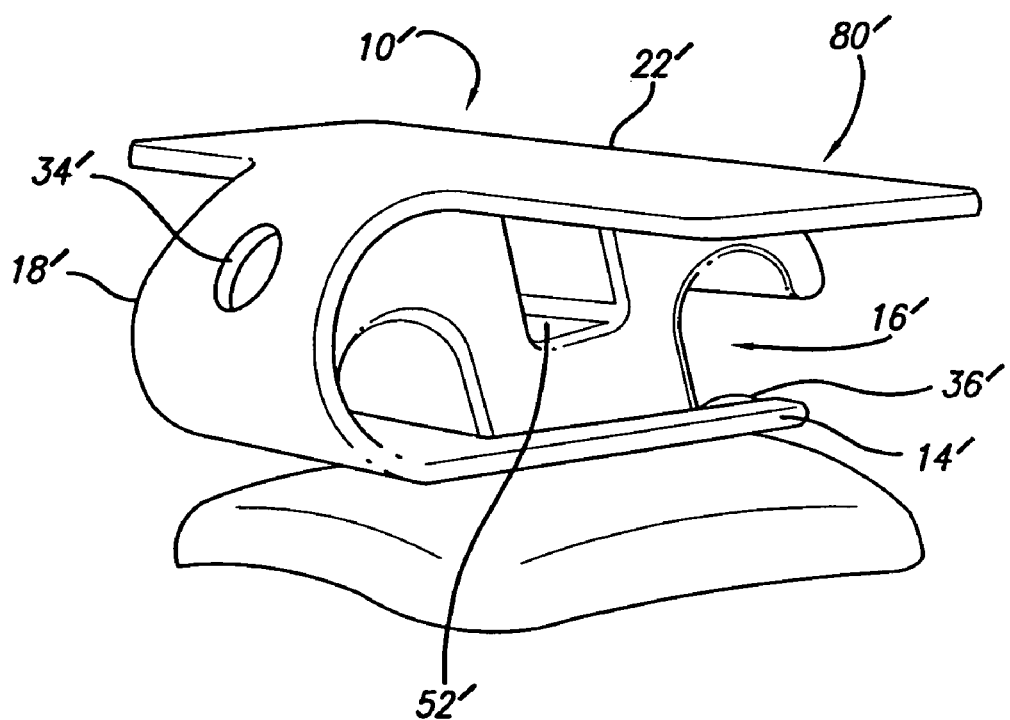
FIG. 10 depicts a perspective view of a single wing orthodontic bracket assembly with the self-ligating clip in a locked-closed position.
Figure 11:
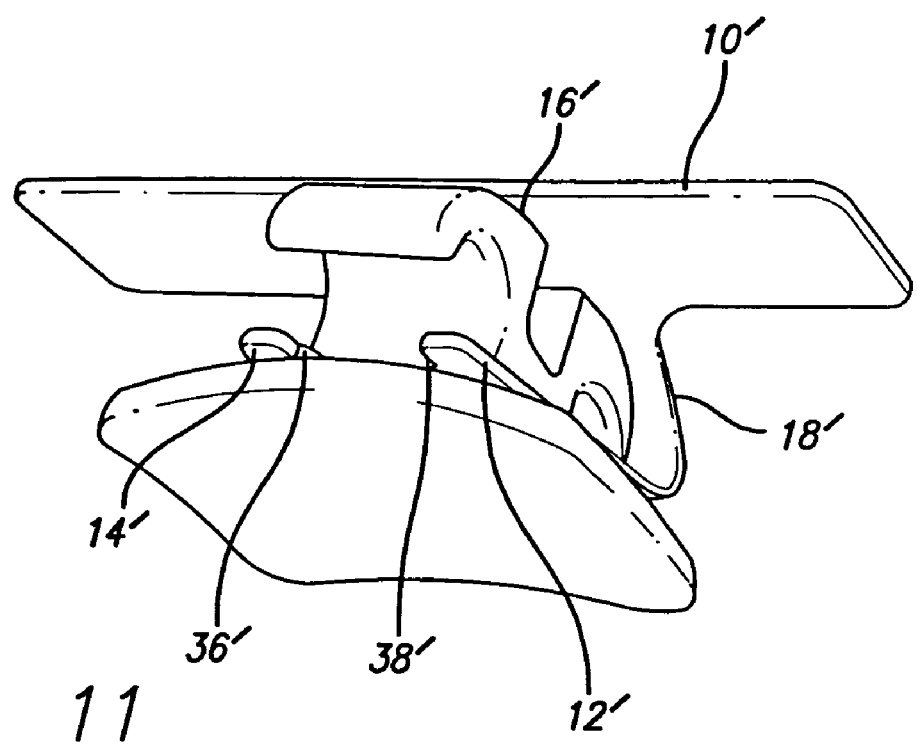
FIG. 11 depicts a partial bottom view of a single wing orthodontic bracket assembly with the self-ligating clip in the locked-closed position.
Figure 12:
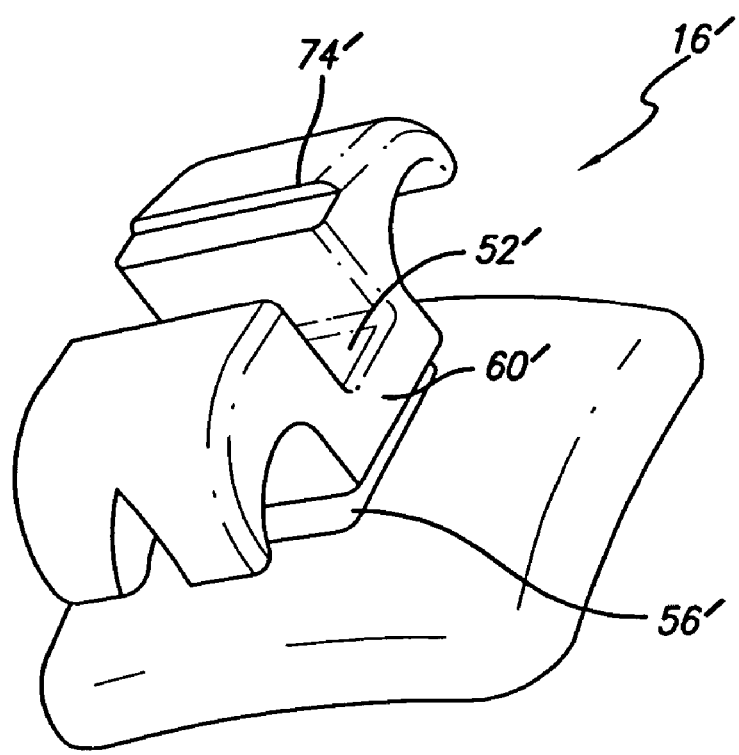
FIG. 12 depicts a perspective view of a single wing orthodontic bracket assembly.
Figure 13:
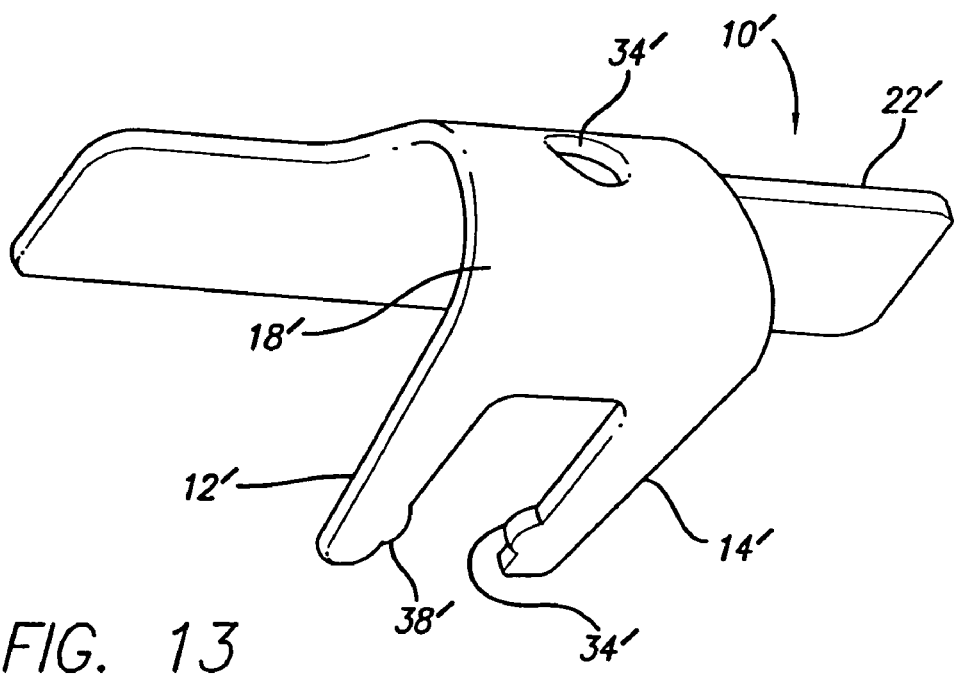
FIG. 13 is a bottom perspective view of the self-ligating clip for use with a single tie-wing orthodontic bracket.
Figure 14:
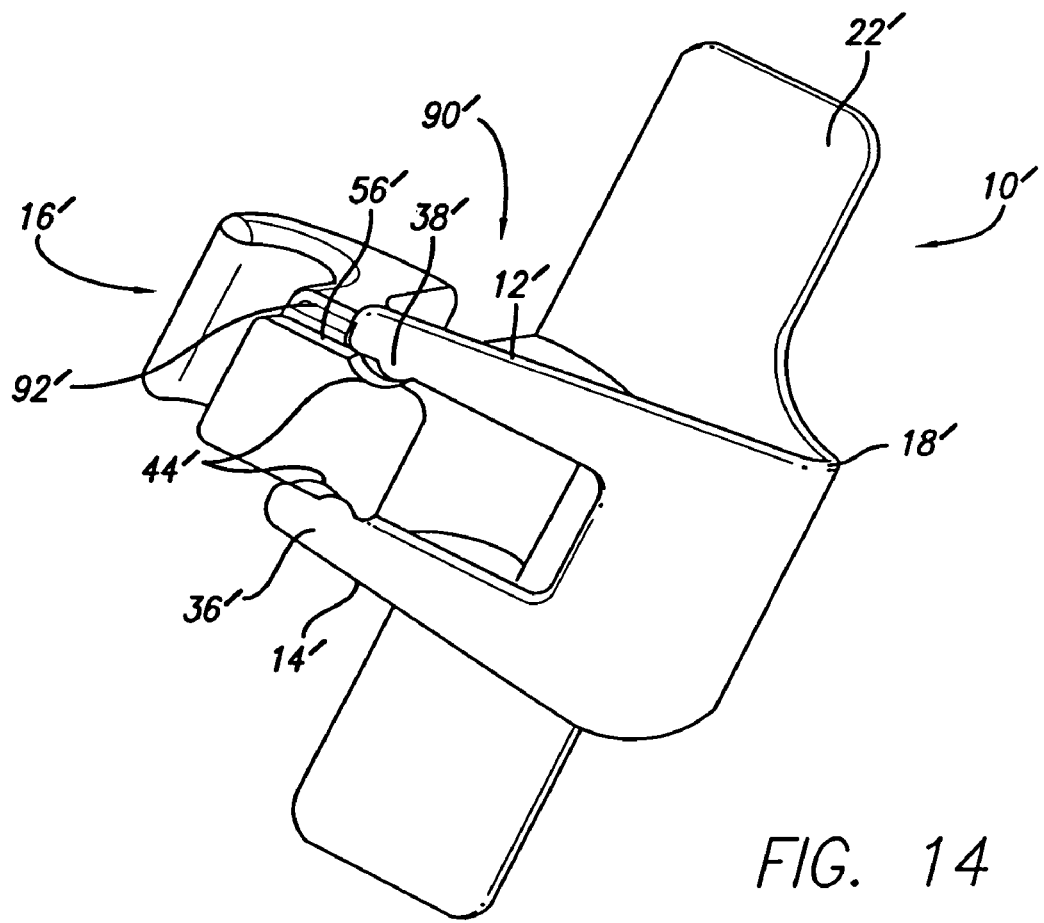
FIG. 14 depicts a bottom view of a single tie-wing orthodontic bracket assembly where the self-ligating clip is in the locked-open position.
Figure 15:
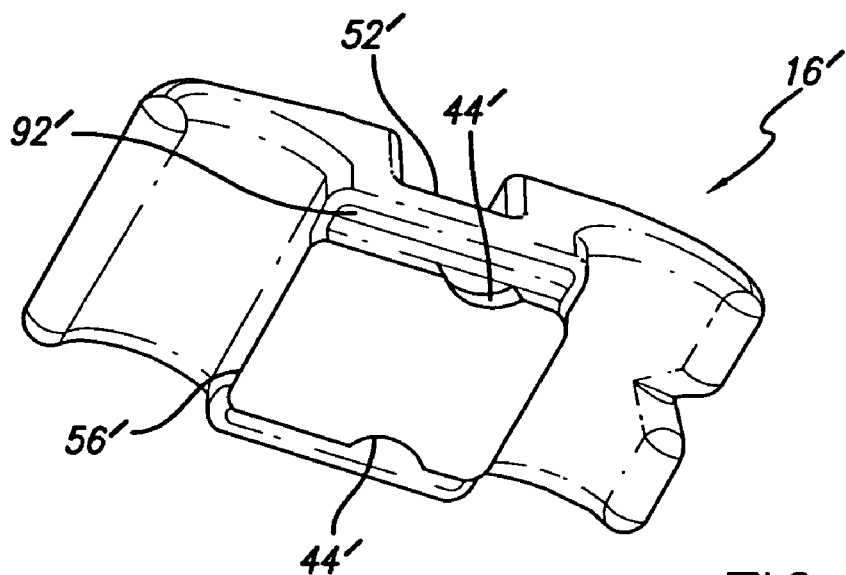
FIG. 15 depicts a bottom view of a single wing orthodontic bracket without a base pad further depicting detents used for locking the clip (not shown) in the locked-open position.
Figure 16:
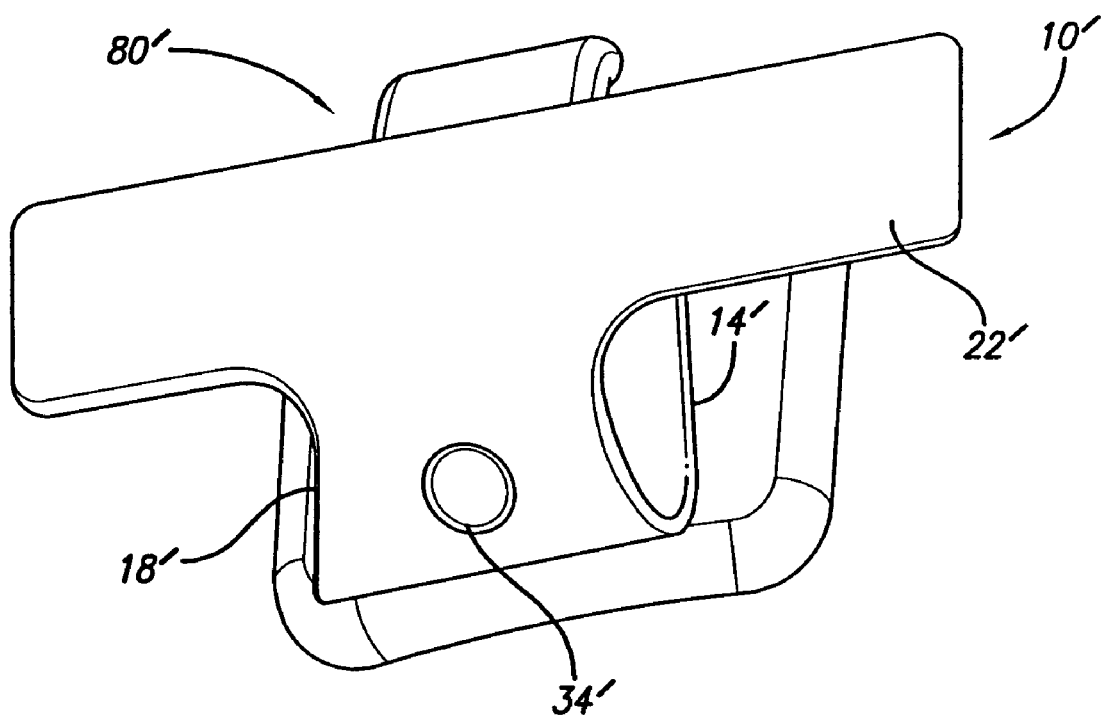
FIG. 16 is a top perspective view of a single tie-wing orthodontic bracket assembly showing the self-ligating clip in the locked-closed position.
Figure 17:
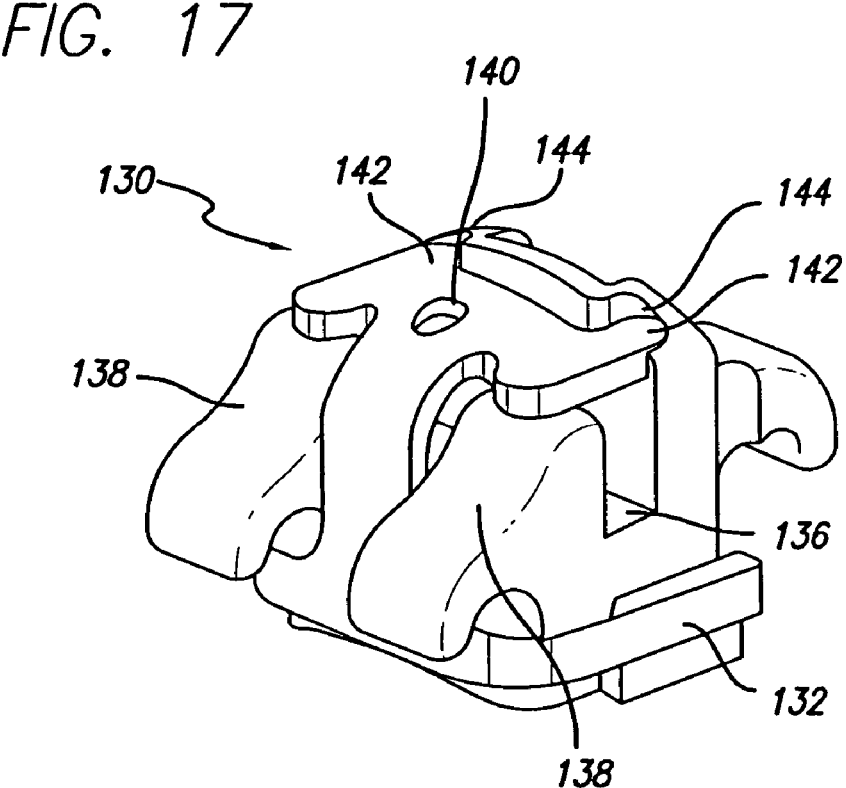
FIG. 17 is a perspective view of one embodiment of an orthodontic clip with a self-ligating clip mounted thereon.
Figure 18:
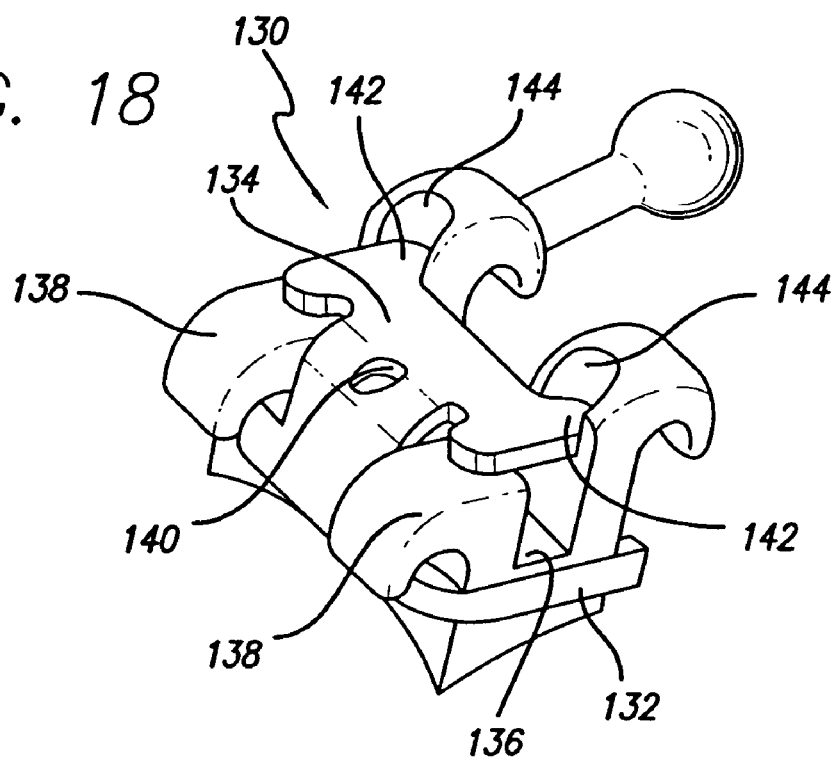
FIG. 18 is a perspective view of one embodiment of an orthodontic clip with a self-ligating clip mounted thereon.

In order to move the clip of the present bracket design from a locked-closed position toward a locked-open position, a scaler or explorer 100 is inserted into the labial aperture 34 of the clip 10, as shown in FIGS. 8A-8B. The use of a conventional sharp-pointed explorer or scaler 100 requires two motions to move the clip 10 from its locked-closed position 80 to its locked-open position 90. First, as the tip 102 of the scaler enters the clip aperture 34 located on the labial surface 104 of the clip, the tapered configuration of the scaler tip 102 working against the clip aperture causes a preloading of the clip in an opening or occlusal direction. This occurs as the tapered scaler tip wedges between the top edge 106 of the occlusal bracket body wall 108 and the inside surface 110 of the aperture. At this point, the clip becomes loaded in the opening direction as the clip spine 18 flexes occlusally and as the tip of the scaler travels lingually. The tip of the scaler continues moving lingually to enter the lingual aperture 35 and comes to a stop as it contacts the labial surface of the bracket-bonding pad 112. As the scaler handle is moved gingivally the arms 12,14, spread outward so that the paws 36,38 release from locking corners 66,68 and the crossbar riser 21 portions of the clip are moved occlusally. Such a movement of the clip entails the highest forces of the opening process because it outwardly loads the paws as they camingly spread apart in order to disengage from the locking corners 66,68 of the bracket body 60. Once the clip paws have disengaged from the closed-position locking corners and the clip is in transit, the forces required to move it to the locked-open position are lower.

With continued reference to FIGS. 8A-8B, the second motion of the opening process is a reverse of the first. To complete the opening process, the tip 102 of the scaler 100 is lifted slightly to come out of the lingual aperture 35 so that it rides on the labial surface of the stemum. The instrument is rotated occlusally. As the handle of scaler 100 is moved occlusally the tip 102 of the scaler lodges at a corner point 114 defined by the labial surface of a clip stemum 116 and a lingual edge 118 formed by the intersection of the clip undercut ceiling 120 and the occlusal bracket body wall 108. With the fulcrum then becoming the tip of the scaler located as described, an occlusal motion of the instrument causes occlusally directed forces to be directed against the labial aperture 34 by the shank of the scaler tip. An occlusally directed motion of the handle of the explorer 100 will wrench the clip substantially open if not fully open. Should the angles and the relative diameters of the particular bracket's labial aperture and the shank of the scaler tip preclude further movement, the scaler tip can be removed from the clip altogether and used to manually push the clip in the direction toward the open position.

As the clip 10 reaches the locked-open position 90, the outwardly-loaded paws 36,38 of the clip arms 12,14 will aggressively pop inward and fall concentrically into the locked-open position detents 44 located at predetermined positions along the mesial and distal clip transport way walls 56.

In one embodiment, during the various movements involving the opening of the clip 10 via the use of a scaler or explorer 100, the tip 102 engages various features of the bracket 16 and the clip 10. To facilitate these steps and to serve as a guide for the scaler tip in finding the various objectives on the inside surfaces of the clip, an opening groove (FIG. 5) is provided and is located centrally on the occlusal bracket body wall 108. The opening groove helps the dental practitioner actuate the clip by centering the instrument tip as it moves from the initial opening position in the lingual aperture 34 of the clip to the secondary position; the edge formed by the intersection of the clip undercut ceiling 120 and the occlusal bracket body wall 108. The vertically oriented groove bisects this corner.

The occlusal corners, defined by the intersection of the transport ways and the occlusal clip undercut wall of the bracket body 60 are rounded to matingly accommodate the inside corner formed between the arms 12,14 and the crossbar riser-portion 21 or the crossbar and the arms of the clip when the assembly is in the locked-closed position 80.

According to the present invention, the occlusal corners are rounded for a second reason: As described in the foregoing, an archwire must be capable of wide deflections during early phases of treatment. In some cases, a wire may only partially enter the archslot 52 and it may be ligated to only one of the two tie-wing sets rather than both. For these reasons and others, an orthodontist might opt to completely remove the clip 10 from the bracket for a period of time. Later, after the teeth have responded to the physiological forces of treatment, the clip may be reinstalled. At the time of re-installing of the clip, the occlusal corners and specifically the rounded configuration of those corners facilitates re-installation of the clip onto the bracket. In order to re-install a clip, the tips 39 of the clip arms 12,14 are simply brought into aligned orientation with the clip transport ways 56 on the occlusal side 108 of the bracket. This may be accomplished using tweezers or other standard dental instruments. The tip 39 of the arms, which are those portions extending gingivally beyond the paws 36,38, is directed to enter the clip transport way 56. Firm gingivally-directed pressure is exerted to force the paws outward around the occlusal corners, which is facilitated by the roundness referred to above. Once the paws have entered the transport ways, the clip is moved further gingivally and into the normal operating range between the locked closed and locked open positions.

Referring to FIGS. 9-16, a single tie-wing orthodontic bracket and self-ligation clip assembly of the present invention is shown. The basic structure of the self-ligating clip is substantially the same for the single tie-wing bracket shown in FIGS. 9-16 as for the twin tie-wing bracket shown in FIGS. 1-8. The reference numbers in FIGS. 9-16 are the same as those used for like structures in FIGS. 1-8 only the reference numbers have a prime in FIGS. 9-16.

Alternative embodiments of the clip with various designs of orthodontic brackets are shown in FIGS. 17-28. In one embodiment, shown in FIG. 17, clip 130 has arms 132 similar to those disclosed herein. In this embodiment, slot cap 134 covers the archslot 136 and extends over the labial surface of occlusal tie wings 138. Aperture 140 extends through slot cap 134 to provide an opening for a scaler or similar type of device to open and close the clip 130 as previously described herein. In this embodiment, clip 130 has protrusions 142 that extend into indentations 144 in the labial surface of the bracket body to help secure the clip in the locked closed position. In the embodiment shown in FIG. 18, the clip 130 is substantially the same as that shown in FIG. 17, but the orthodontic bracket has a slightly different design. Thus, clip 130 can be used with numerous types of orthodontic brackets and different designs to achieve the same purpose, that is to secure the archwire in the archwire slot effortlessly and with a minimal amount of time on the part of the orthodontist when changing out archwires.

Figure 19:
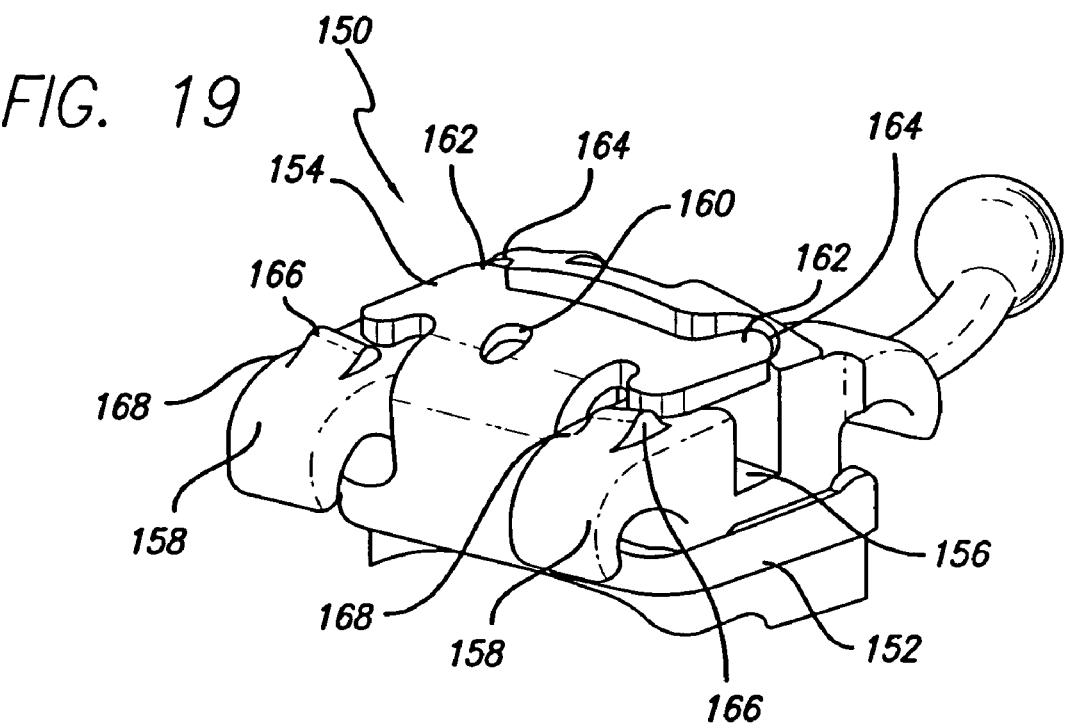
FIG. 19 is a perspective view of an orthodontic bracket with a self-ligating clip mounted thereon in the locked closed position and depicting locking ridges to hold the clip in place.
Figure 20:
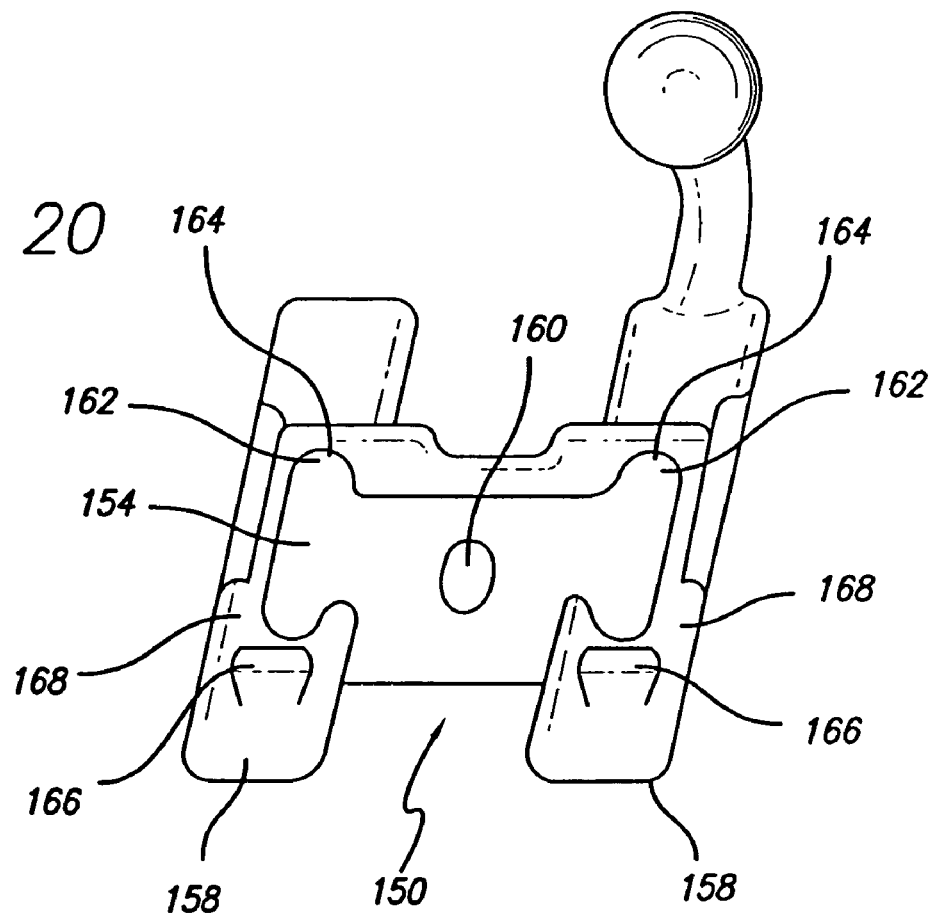
FIG. 20 is a top view of the orthodontic bracket assembly with the self-ligating clip of FIG. 19.
Figure 23A:
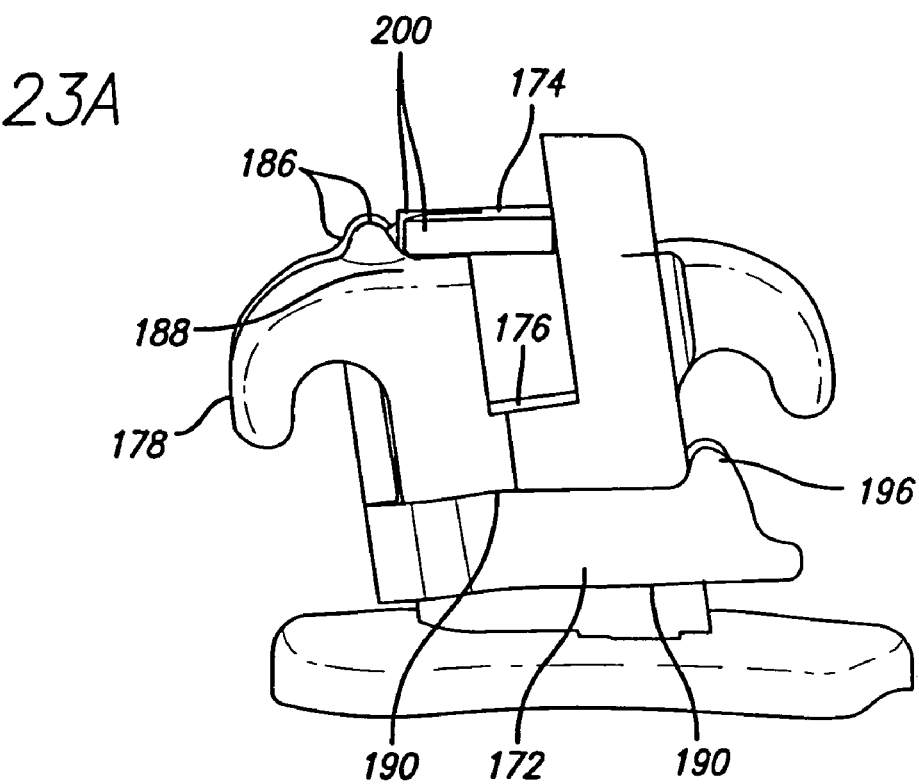
FIG. 23A is a side view of an orthodontic bracket assembly having a self-ligating clip positioned in the clip locked position and covering the archwire slot.
Figure 23B:
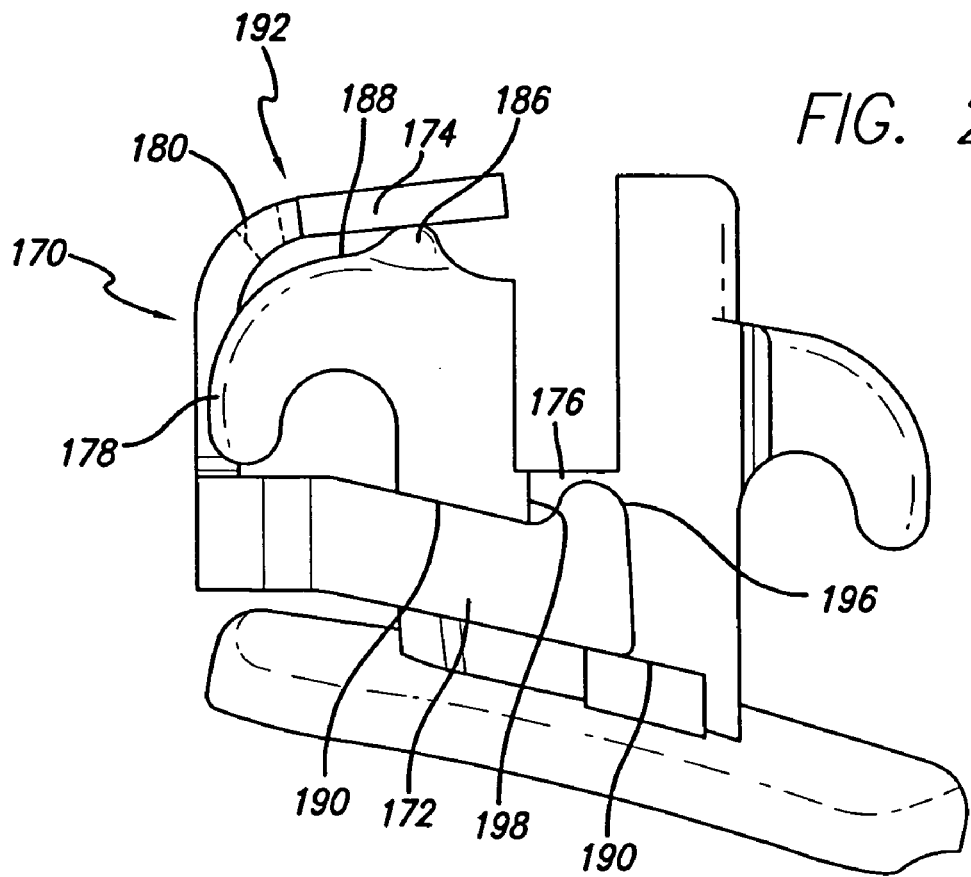
FIG. 23B is a side view depicting the orthodontic bracket assembly having a self-ligating clip in the clip open position.
Figure 24:
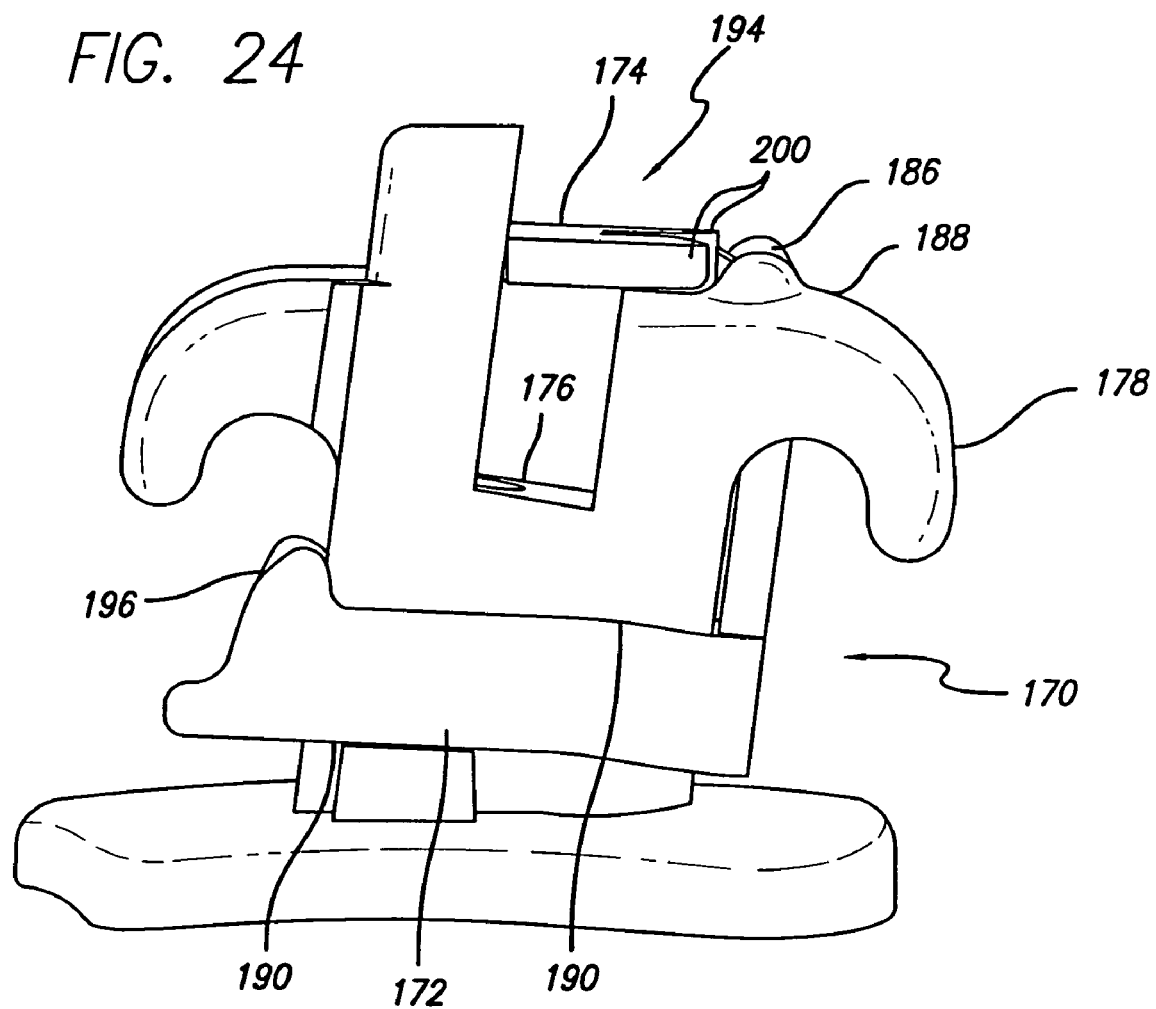
FIG. 24 is a side view of an orthodontic bracket assembly having a self-ligating clip positioned in the clip locked position.
Figure 25A:
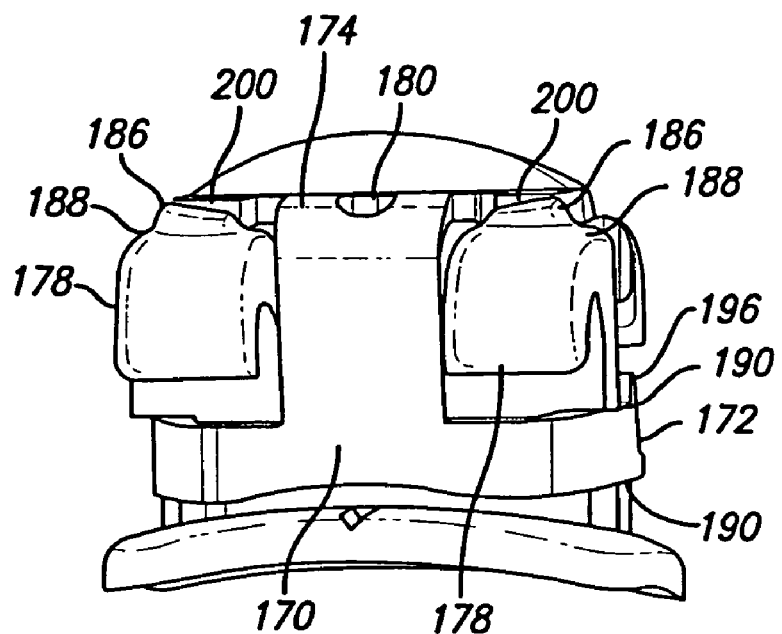
FIGS. 25A and 25B are occlusal partial perspective view of an orthodontic bracket assembly having a self-ligating clip positioned in the locked closed position.
Figure 25B:
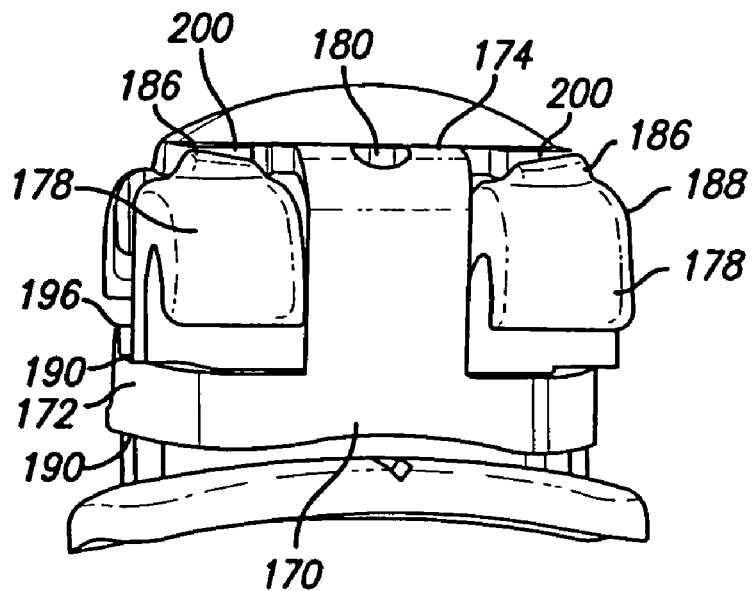
Figure 26:
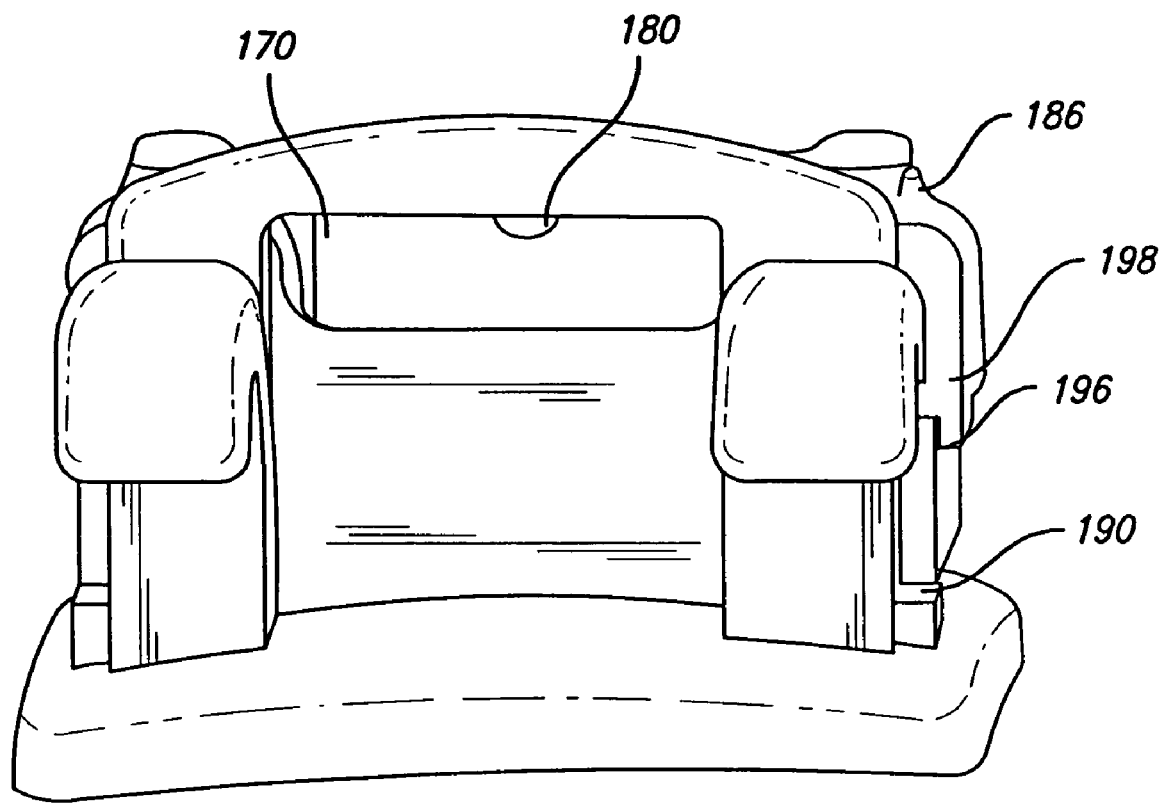
FIG. 26 is a gingival partial perspective view of an orthodontic bracket assembly depicting a self-ligating clip positioned in the clip open position.
Figure 27A:
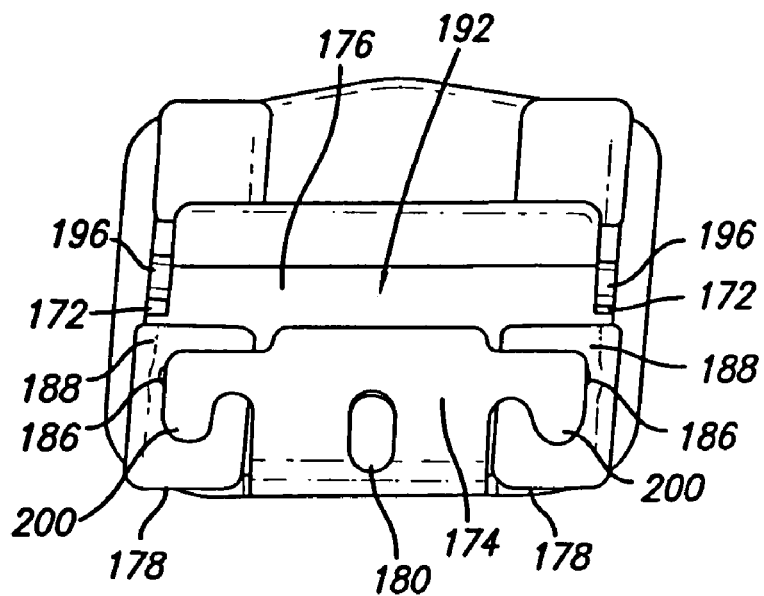
FIG. 27A is the top view of an orthodontic bracket assembly depicting a self-ligating clip positioned in a clip open position.
Figure 27B:
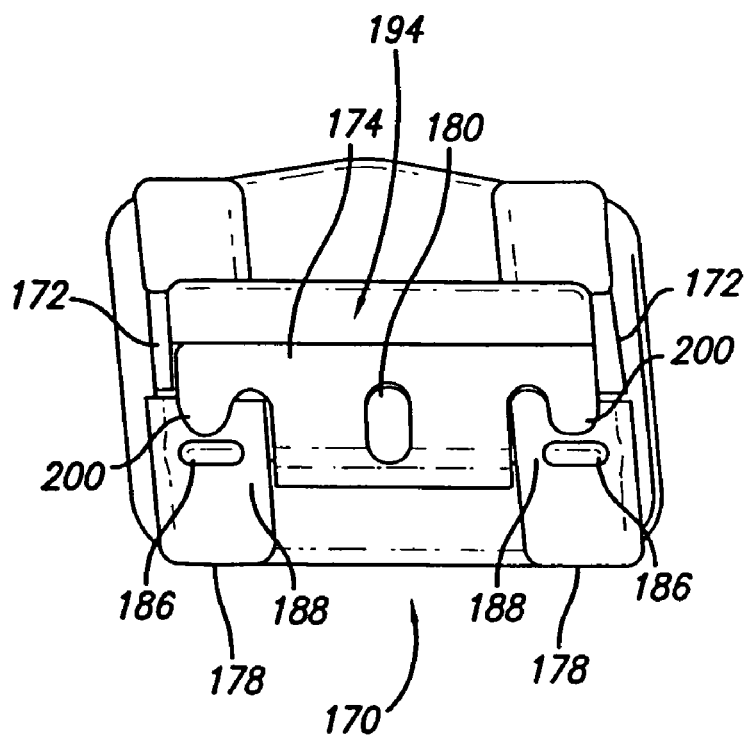
FIG. 27B is a top view of an orthodontic bracket assembly depicting a self-ligating clip positioned in a clip locked position.
Figure 30A:
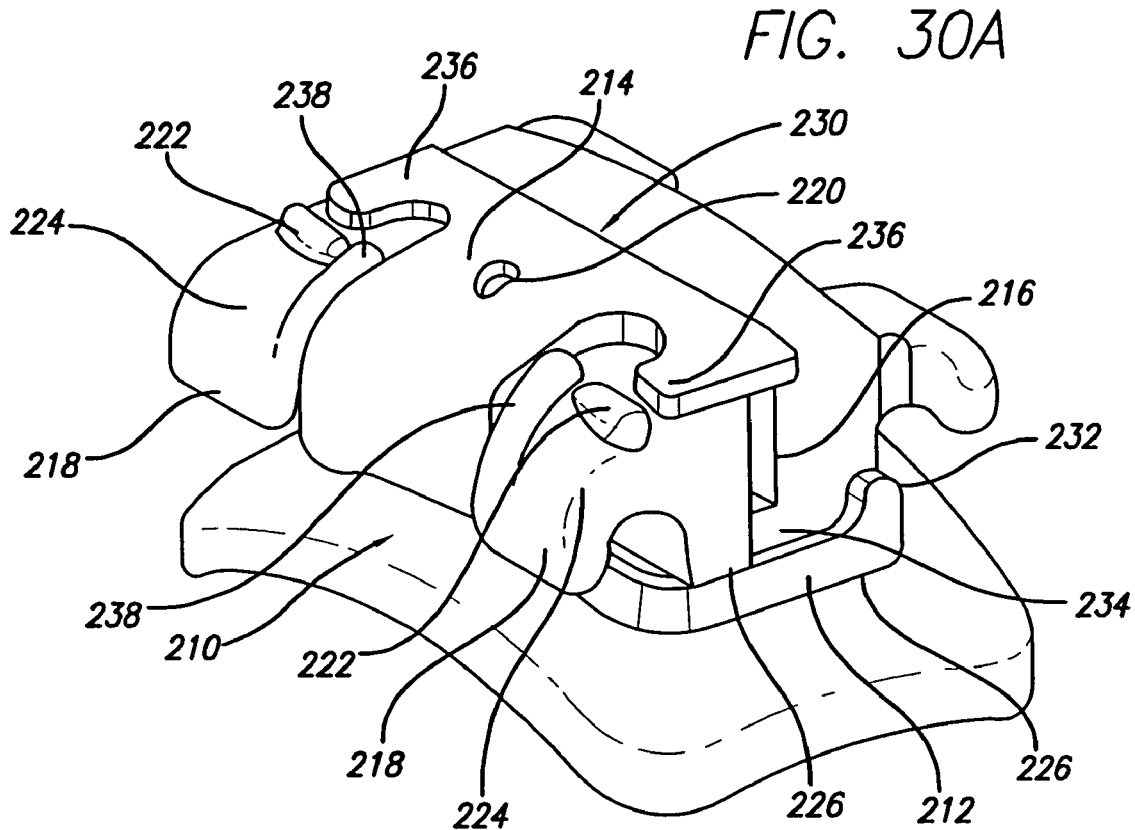
FIG. 30A is a top perspective view of an orthodontic bracket assembly depicting a self-ligating clip positioned in a clip open position.
Figure 30B:
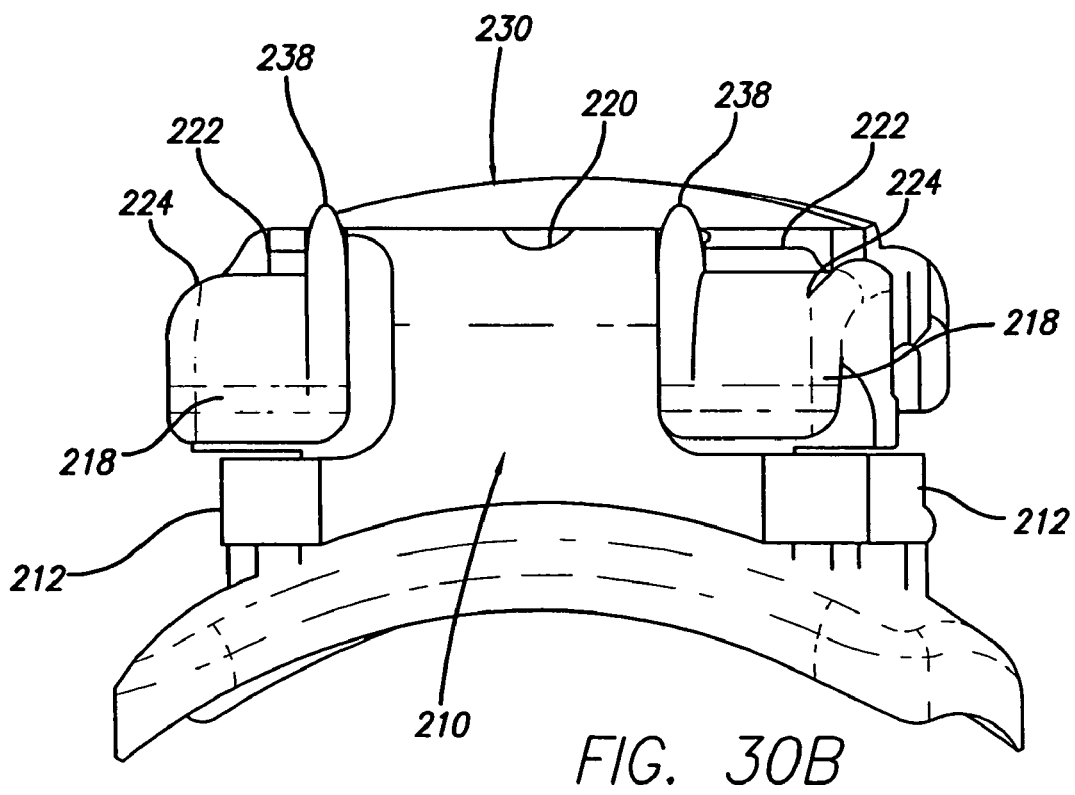
FIG. 30B is a front end view of the orthodontic bracket assembly of FIG. 30A.

In another embodiment, as shown in FIGS. 19 and 20, clip 150 has a pair of arms 152 that slide along the base of the bracket to hold the clip in the bracket. The slot cap 154 covers the archslot 156 as previously disclosed. The occlusal tie wings 158 provide a labial surface upon which the clip 150 slides over and rests on. Aperture 160 in the slot cap 154 provides an opening for the scaler to open and close clip 150. The clip 150 also has protrusions 162 that engage indentations 164 in the body of the bracket near the archslot 156 in order to better secure the clip 150 in the locked closed position. In this embodiment, locking ridges 166 are positioned on the labial surface 168 of the occlusal tie wings 158 in order to prevent clip 150 from inadvertently moving toward the open position. It is only when the orthodontist uses a scaler as previously described to insert through the aperture 160 and move the scaler to open clip 150 that the clip slides over the top of locking ridges 166 so that the clip is in the open position 192.

In another embodiment, shown in FIGS. 21-28, clip 170 has a pair of arms 172 that slide along the base of the bracket to hold the clip in the bracket. The slot cap 174 covers the archslot 176 as previously disclosed. The occlusal tie wings 178 provide a labial surface upon which the clip 170 slides over and rests on. Aperture 180 in the slot cap 174 provides an opening for inserting the scaler to open and close clip 170. In this embodiment, locking ridges 186 are positioned on the labial surface 188 of the occlusal tie wings 178 in order to prevent clip 170 from inadvertently moving toward the open position. It is only when the orthodontist uses a scaler as previously described to insert through the aperture 180 and move the scaler to open clip 170 that the clip slides over the top of locking ridges 186 so that the clip is in the open position. In keeping with the invention, the arms 172 slide along transport ways 190 and are shown in FIG. 21 in a clip open position 192. At the distal end of arms 172 is a tab 196 that engages with wall 198 of the occlusal tie wings 178. As clip 170 is moved from its clip open position 192 to its clip locked position 194, arms 172 will slide along transport ways 190 as protrusions 200 on clip 170 slide over locking ridges 186 to firmly lock the slot cap 174 over the archslot 176. Similarly, as clip 170 is moved from the clip locked position 194 to the clip open position 192, arms 172 slide along transport ways 190 until tabs 196 engage wall 198 and protrusions 200 on clip 170 slide over the top of locking ridges 186. Tabs 196 prevent the clip 170 from completely disengaging from the orthodontic bracket since the tabs engage wall 198 and the resiliency of the clip 170 provides a spring force on the labial surface 188 on occlusal tie wings 178. As previously described, the orthodontist can use a scaler or similar device to insert through aperture 180 in order to move clip 170 from the clip open position 192 to the clip locked position 194, and vice versa.

Figure 31A:
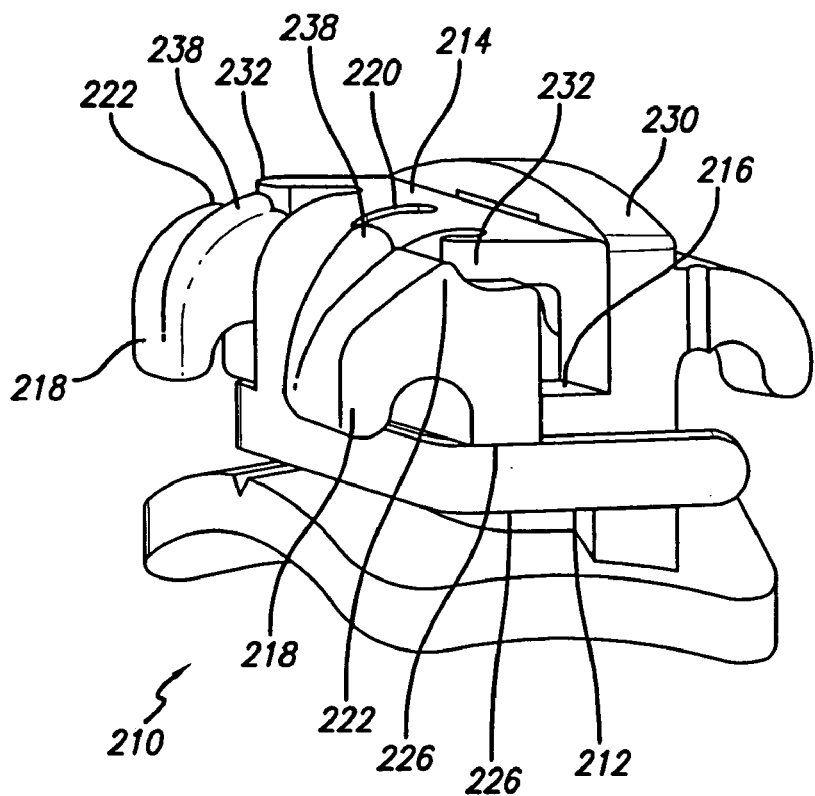
FIG. 31A is a top perspective view of an orthodontic bracket assembly depicting a self-ligating clip position in a clip closed position.
Figure 31B:
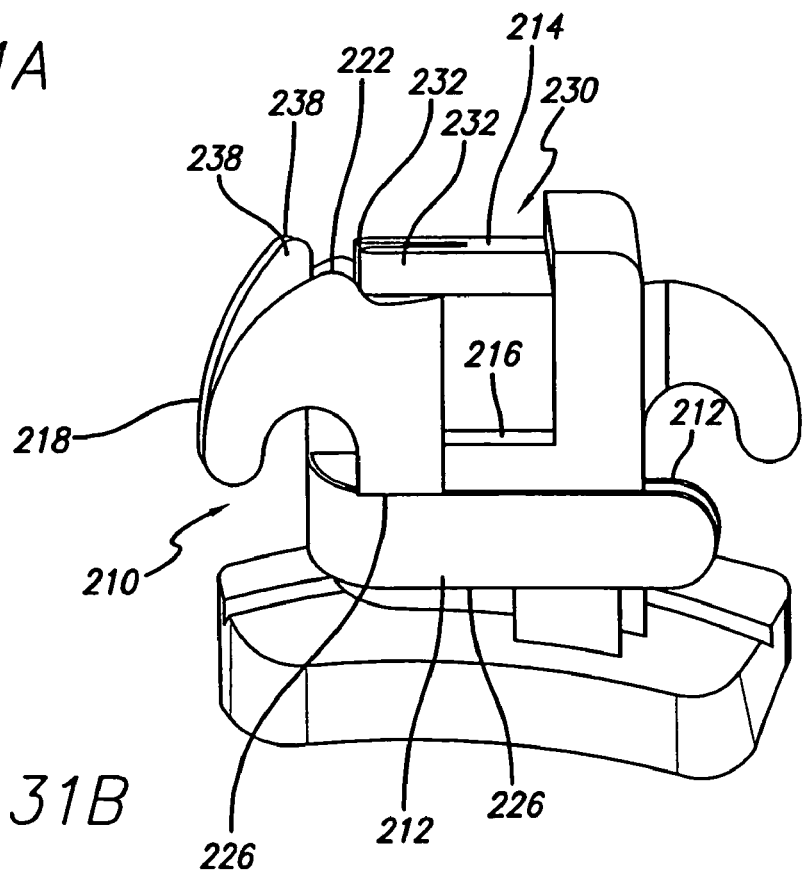
FIG. 31B is a right side view of the orthodontic bracket assembly of FIG. 31A depicting the self-ligating clip positioned in a clip closed position.
Figure 31C:
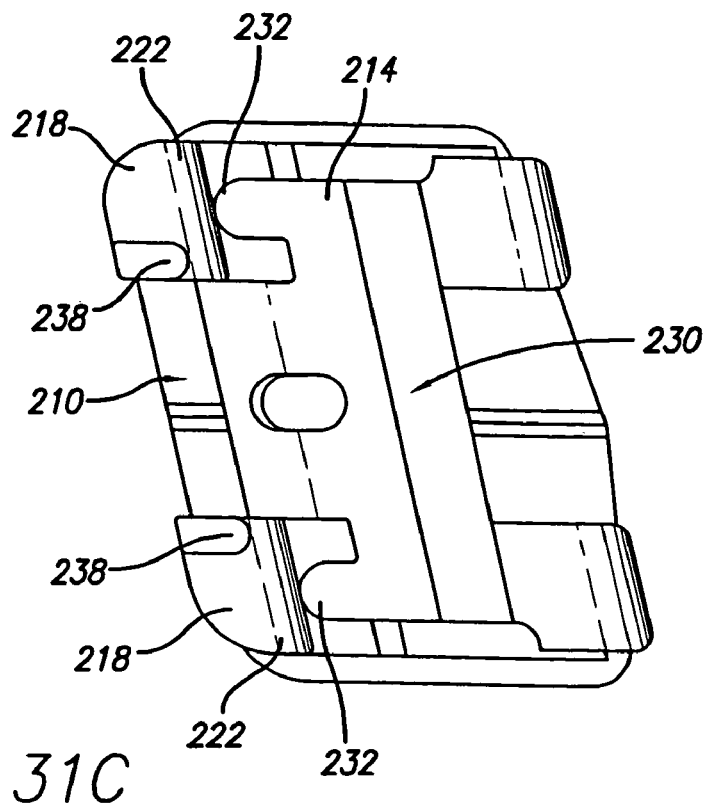
FIG. 31C is a top view of an orthodontic bracket assembly depicting a self-ligating clip in a clip closed position.
Figure 31D:
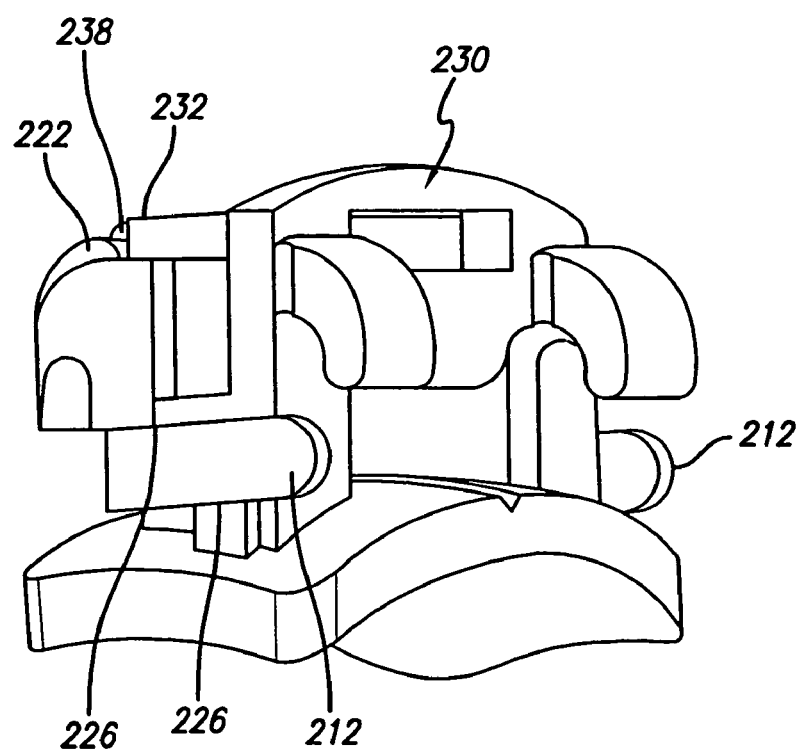
FIG. 31D is a side perspective view of an orthodontic bracket assembly depicting a self-ligating clip positioned in a clip closed position.
Figure 31E:
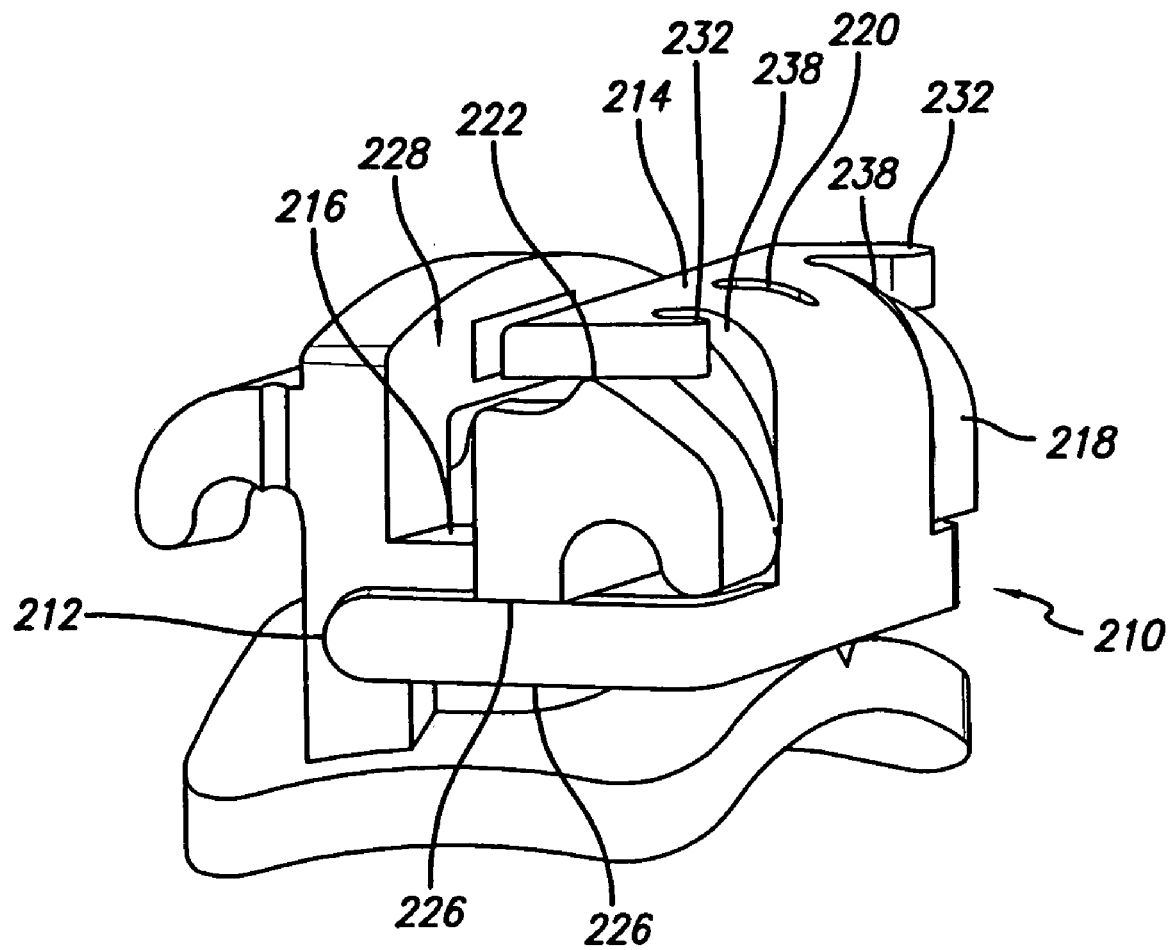
FIG. 31E is a side perspective view of an orthodontic bracket assembly of a self-ligating clip positioned in a clip open position.

In another embodiment, shown in FIGS. 29A-31E, clip 210 has a pair of arms 212 that slide along the base of the bracket to hold the clip in the bracket. The slot cap 214 covers the archslot 216 as previously disclosed. The occlusal tie wings 218 provide a labial surface upon which the clip 210 slides over and rests on. Aperture 220 in the slot cap 214 provides an opening for inserting the scaler to open and close clip 210. In this embodiment, locking ridges 222 are positioned on the labial surface 224 of the occlusal tie wings 218 in order to prevent clip 210 from inadvertently moving toward the open position. It is only when the orthodontist uses a scaler as previously described to insert through the aperture 220 and move the scaler to open clip 210 that the clip slides over the top of locking ridges 222 so that the clip is in the open position. In keeping with the invention, the arms 212 slide along transport ways 226 and are shown in FIGS. 29A, 29B, and 31E in a clip open position 228. At the distal end of arms 212 is a tab 232 that engages with wall 234 of the occlusal tie wings 218. As clip 210 is moved from its clip open position 228 to its clip locked position 230, arms 212 will slide along transport ways 226 as protrusions 236 on clip 210 slide over locking ridges 222 to firmly lock the slot cap 214 over the archslot 216. Similarly, as clip 210 is moved from the clip locked position 230 to the clip open position 228, arms 212 slide along transport ways 226 until tabs 232 engage wall 234 and protrusions 236 on clip 210 slide over the top of locking ridges 222. Tabs 232 prevent the clip 210 from completely disengaging from the orthodontic bracket since the tabs engage wall 234 and the resiliency of the clip 212 provides a downward spring force on the labial surface 224 on occlusal tie wings 218. As previously described, the orthodontist can use a scaler or similar device to insert through aperture 220 in order to move clip 210 from the clip open position 228 to the clip locked position 230, and vice versa.

To further secure the clip 210 on the orthodontic bracket, and to ensure that the clip does not unintentionally dislodge when in the clip open position 228, clip travel stop 238 engages the clip as the clip is opened and limits how far the clip moves toward the clip open position 228. The clip travel stop 238 is a raised stop positioned on labial surface 224 and next to the locking ridges 222 and it engages the clip 210 to limit clip movement to the clip open position 228. Importantly, clip travel stop 238 prevents the clip from traveling past the occlusal/gingival profile of the bracket tie wings.

With respect to all of the foregoing embodiments of the clip, it is important to form the clip so that it has a resiliency or springiness so that it will firmly lock in the locked closed position and hold the archwire in the archwire slot until such time as the orthodontist uses a scaler or other instrument to move the clip to an open position. The thickness of the clip is one factor in determining how much force the clip is able to apply when it is in the locked closed position. Accordingly, it is preferred that the clip having substantially uniform thickness in the range of about 0.0004 inch to about 0.012 inch, and more preferably the clip has a substantially uniform thickness in the range of about 0.007 inch to about 0.009 inch. In one embodiment, the clip has a substantially uniform thickness of about 0.009 inch. A clip having a relatively greater thickness provides an increase in stiffness and its ability to firmly stay locked in the locked closed position and firmly open in the open position.

With respect to all of the embodiments of the orthodontic bracket disclosed herein, the bracket can be used without the clip as orthodontic brackets normally would be used to treat a patient. The locking ridges disclosed herein can act as a handle on the bracket for use without a clip in a case where, for example, there is a severely angled cuspid and to aid in bringing it into position, the orthodontist can loop a spring around a locking ridge. Also, the orthodontic bracket disclosed herein can be used without a clip where a crimpable hook is placed in the center of the bracket in between the locking ridges which can be used to aid in retraction.

Although the present invention has been described in the context of preferred embodiments, it is not intended to limit the invention to the embodiments described. Accordingly, modifications may be made to the disclosed embodiments without departing from the spirit and scope of the invention. Accordingly, various features and aspects of the disclosed embodiments may be combined with or substituted for one another in order to form varying modes of the invention.

What is claimed:

1. An orthodontic bracket assembly, comprising:
    an orthodontic bracket having occlusal and gingival tie wings;
    a clip having a generally U-shaped configuration and having a first arm and a second arm;
    the first arm and the second arm slidingly engage a transport ways;
    a cross-bar on the clip connecting the arms and a central spine extending from the cross-bar to a cap;
    an aperture positioned in the cap to facilitate opening and closing the clip into engagement with the orthodontic bracket to retain an archwire in an archslot; and
    protrusions on the clip to slidingly engage locking ridges on the orthodontic bracket.

2. The assembly of claim 1, wherein the first arm and the second arm each have a tab for engaging the orthodontic bracket.

3. The assembly of claim 2, wherein the tab of the first arm and the second arm engage a wall of the occlusal tie wings to limit travel of the arms.

4. The assembly of claim 1, wherein the clip is configured for low profile.

5. The assembly of claim 1, wherein the locking ridges are positioned on a labial surface of the occlusal tie wings.

6. The assembly of claim 1, wherein the locking ridges have a beveled surface so that the protrusions on the clip can more easily slide onto and over the locking ridges.

7. The assembly of claim 1, wherein a clip travel stop limits travel of the clip when moving from a clip closed position to a clip open position.

8. The device of claim 1, wherein the clip has protrusions for matingly engaging the orthodontic bracket when the clip is in the clip locked position.

9. The device of claim 8, wherein a clip travel stop limits travel of the clip when moving from a clip closed position to a clip open position.

10. An orthodontic bracket assembly, comprising:
    an orthodontic bracket having at least two tie-wings and an archslot in the at least two tie-wings for receiving an archwire;
    a clip for mounting onto the orthodontic bracket, the clip having a first arm and a second arm;
    the orthodontic bracket having a mesial transport way and a distal transport way for slidably receiving the first arm and the second arm;
    the first arm and the second arm each having tabs for engaging a wall of the tie wings so that the clip will remain mounted on the orthodontic bracket when the clip is moved from a clip locked position to a clip open position.

11. The assembly of claim 10, wherein the clip engages a clip travel stop on the orthodontic bracket to releasably cover the archslot.

12. The assembly of claim 10, wherein the tabs of the first arm and the second arm each matingly engage a wall as the clip is moved to the clip open position.

13. The assembly of claim 10, wherein the clip has protrusions that engage locking ridges on a labial surface of the tie wings when the clip is in a clip locked position.

14. The assembly of claim 10, wherein the clip is formed from a metal alloy.

15. The assembly of claim 14, wherein the clip metal alloy is taken from the group of metal alloys consisting of stainless steel, titanium, NP35N, cobalt-chromium, Nitinol, super-elastic alloys, pseudoelastic alloys, and shape-memory alloys.

16. The assembly of claim 10, wherein a clip travel stop limits travel of the clip when moving from a clip closed position to a clip open position.

17. A method of exchanging an archwire in an archwire slot of an orthodontic bracket, comprising:
    providing an orthodontic bracket having a first archwire positioned in an archwire slot, the orthodontic bracket further comprising a clip removably mounted on the orthodontic bracket and having a clip locked position covering the archwire slot and retaining the first archwire in the archwire slot;
    moving the clip from the clip locked position to a clip open position;
    removing the first archwire from the archwire slot and inserting a second archwire in the archwire slot;
    moving the clip from the clip open position to the clip locked position thereby retaining the second archwire in the archwire slot; and
    the orthodontic bracket having locking ridges on a labial surface of occlusal tie-wings, the clip being retained in the clip locked position by the locking ridges; and
    the clip slides over the locking ridges to the clip open position.

18. The method of claim 17, wherein the clip includes a pair of arms that slidingly engage transport ways on the orthodontic bracket as the clip moved from the clip locked position to the clip open position, and vice versa.

19. The method of claim 18, wherein the clip arms have tabs, the tabs engaging a wall of the orthodontic bracket when the clip is moved from the clip locked position to the clip open position thereby limiting the distance the clip can move toward the clip open position.

20. The method of claim 17, wherein the clip engages a clip travel stop when the clip moves from the clip closed position to the clip open position.

* * * * *